US009193593B2

(12) United States Patent
Masel et al.

(10) Patent No.: US 9,193,593 B2
(45) Date of Patent: Nov. 24, 2015

(54) HYDROGENATION OF FORMIC ACID TO FORMALDEHYDE

(71) Applicant: Dioxide Materials, Inc., Champaign, IL (US)

(72) Inventors: Richard I. Masel, Champaign, IL (US); Zheng Richard Ni, Champaign, IL (US); Qingmei Chen, Savoy, IL (US); Brian A. Rosen, Champaign, IL (US)

(73) Assignee: Dioxide Materials, Inc., Boca Raton, FL (US)

( * ) Notice: Subject to any disclaimer, the term of this patent is extended or adjusted under 35 U.S.C. 154(b) by 114 days.

(21) Appl. No.: 13/775,245

(22) Filed: Feb. 24, 2013

(65) Prior Publication Data
US 2014/0239231 A1  Aug. 28, 2014

(51) Int. Cl.
*C01B 31/18* (2006.01)
*C01B 3/22* (2006.01)
*C07C 1/22* (2006.01)
*C07C 45/41* (2006.01)
*C07H 1/00* (2006.01)
*C07C 51/15* (2006.01)

(52) U.S. Cl.
CPC . *C01B 31/18* (2013.01); *C01B 3/22* (2013.01); *C07C 1/22* (2013.01); *C07C 45/41* (2013.01); *C07C 51/15* (2013.01); *C07H 1/00* (2013.01)

(58) Field of Classification Search
CPC ............ C01B 3/22; C01B 31/18; C07C 1/22; C07C 45/41; C07C 51/15; C07H 1/00
USPC ............................ 568/373; 562/598; 585/324
See application file for complete search history.

(56) References Cited

U.S. PATENT DOCUMENTS

| | | |
|---|---|---|
| 1,919,850 A | 7/1933 | Luscher |
| 2,511,198 A | 6/1950 | Engel |
| 2,996,359 A | 8/1961 | Mossman et al. |
| 3,959,094 A | 5/1976 | Steinberg |
| 4,207,151 A | 6/1980 | Franke et al. |
| 4,240,882 A | 12/1980 | Ang et al. |
| 4,315,753 A | 2/1982 | Bruckenstein et al. |
| 4,474,652 A | 10/1984 | Brown et al. |
| 4,523,981 A | 6/1985 | Ang et al. |
| 4,545,872 A | 10/1985 | Sammells et al. |
| 4,595,465 A | 6/1986 | Ang et al. |
| 4,608,132 A | 8/1986 | Sammells |
| 4,608,133 A | 8/1986 | Morduchowitz et al. |
| 4,609,440 A | 9/1986 | Frese, Jr. et al. |
| 4,609,441 A | 9/1986 | Frese, Jr. et al. |
| 4,620,906 A | 11/1986 | Ang |
| 4,668,349 A | 5/1987 | Cuellar et al. |
| 4,673,473 A | 6/1987 | Ang et al. |
| 4,756,807 A | 7/1988 | Meyer et al. |
| 4,771,708 A | 9/1988 | Douglass, Jr. |
| 4,789,442 A | 12/1988 | Nakagawa et al. |
| 4,818,353 A | 4/1989 | Langer et al. |
| 4,879,070 A | 11/1989 | Kent |
| 4,968,393 A | 11/1990 | Mazur et al. |
| 5,064,733 A | 11/1991 | Krist et al. |
| 5,071,526 A | 12/1991 | Pletcher et al. |
| 5,089,661 A | 2/1992 | Maspero et al. |
| 5,206,433 A | 4/1993 | Hohenschutz et al. |
| 5,284,563 A | 2/1994 | Fujihira et al. |
| 5,294,740 A | 3/1994 | Kiefer et al. |
| 5,334,759 A | 8/1994 | Lippert et al. |
| 5,382,332 A | 1/1995 | Fujihira et al. |
| 5,639,910 A | 6/1997 | Ikariya et al. |
| 5,709,789 A | 1/1998 | Shay et al. |
| 5,763,622 A | 6/1998 | Podszun et al. |
| 5,804,045 A | 9/1998 | Orillon et al. |
| 5,879,915 A | 3/1999 | Loubiere et al. |
| 5,928,806 A | 7/1999 | Olah et al. |
| 5,952,540 A | 9/1999 | Lee et al. |
| 6,024,855 A | 2/2000 | Sharifian et al. |
| 6,429,333 B1 | 8/2002 | Saari et al. |
| 6,660,680 B1 | 12/2003 | Hampden-Smith et al. |

(Continued)

FOREIGN PATENT DOCUMENTS

| | | |
|---|---|---|
| CA | 1272180 A | 7/1990 |
| CA | 2821642 A1 | 6/2012 |

(Continued)

OTHER PUBLICATIONS

CAS Registry, CAS No. 919104-58-9-8, Entered in STN Feb. 2, 2007, p. 1.*
Chinese Office Action issued on Aug. 5, 2014 in connection with Chinese Application No. 201180023851.2.
Arenz, M. et al., "The effect of the particle size on the kinetics of CO electrooxidation on high surface area Pt catalysts", Journal of the American Chemical Society 127 (2005), pp. 6819-6829.
Azuma, M. et al., "Electrochemical reduction of carbon dioxide on various metal, electrodes in low-temperature aqueous KHCO3 media", J. Electrochem. Soc. 137 (1990), pp. 1772-1778.

(Continued)

*Primary Examiner* — Paul A Zucker
*Assistant Examiner* — Mark Luderer
(74) *Attorney, Agent, or Firm* — Corridor Law Group, P.C.

(57) ABSTRACT

An environmentally beneficial process for the production of fuels and chemicals employs carbon dioxide from a natural source or from an artificial chemical source that would otherwise be discharged into the environment. The carbon dioxide is converted to formic acid and the formic acid is then non-biologically converted to fuels and/or chemicals without the intermediate process of hydrogenating the formic acid to methanol or reacting the formic acid with ammonia to form formamide. In the present process, formic acid is converted to one of seven primary feedstocks: formaldehyde, acrylic acid, methane, ethylene, propylene, syngas, and C5-C7 carbohydrates. The formaldehyde, acrylic acid, methane, ethylene, propylene, syngas and/or short chain carbohydrates can either be used directly, or can be converted into a wealth of other products.

5 Claims, 13 Drawing Sheets

(56) References Cited

U.S. PATENT DOCUMENTS

| | | |
|---|---|---|
| 6,706,657 B2 | 3/2004 | Commereuc et al. |
| 6,713,649 B1 | 3/2004 | Hladiy et al. |
| 6,841,700 B2 | 1/2005 | Auer et al. |
| 6,849,764 B2 | 2/2005 | Gurkaynak et al. |
| 6,867,329 B2 | 3/2005 | Auer et al. |
| 6,906,222 B2 | 6/2005 | Slany et al. |
| 6,955,743 B2 | 10/2005 | Rousu et al. |
| 6,987,134 B1 | 1/2006 | Gagnon |
| 6,992,212 B2 | 1/2006 | Zehner et al. |
| 7,081,547 B2 | 7/2006 | Fujimoto et al. |
| 7,157,404 B1 | 1/2007 | Jun et al. |
| 7,241,365 B2 | 7/2007 | Auer et al. |
| 7,253,316 B2 | 8/2007 | Pastre et al. |
| 7,323,593 B2 | 1/2008 | Adami et al. |
| 7,351,860 B2 | 4/2008 | Adami et al. |
| 7,420,088 B2 | 9/2008 | Karl et al. |
| 7,459,590 B2 | 12/2008 | Olah et al. |
| 7,479,570 B2 | 1/2009 | Ogo et al. |
| 7,605,293 B2 | 10/2009 | Olah et al. |
| 7,608,743 B2 | 10/2009 | Olah et al. |
| 7,612,233 B2 | 11/2009 | Hauk et al. |
| 7,618,725 B2 | 11/2009 | Masel et al. |
| 7,704,369 B2 | 4/2010 | Olah et al. |
| 8,313,634 B2 | 11/2012 | Bocarsly et al. |
| 8,592,633 B2 | 11/2013 | Cole et al. |
| 2004/0031685 A1 | 2/2004 | Anderson et al. |
| 2006/0096871 A1 | 5/2006 | Manoukian et al. |
| 2006/0234174 A1 | 10/2006 | Burrahm et al. |
| 2006/0235091 A1 | 10/2006 | Olah et al. |
| 2007/0036706 A1 | 2/2007 | Ogo et al. |
| 2007/0045125 A1 | 3/2007 | Hartvigsen et al. |
| 2007/0187247 A1 | 8/2007 | Lackner et al. |
| 2008/0039538 A1 | 2/2008 | Olah et al. |
| 2008/0103040 A1 | 5/2008 | Rodriguez et al. |
| 2008/0223727 A1 | 9/2008 | Oloman et al. |
| 2009/0014336 A1 | 1/2009 | Olah et al. |
| 2009/0016948 A1 | 1/2009 | Young |
| 2009/0169452 A1 | 7/2009 | Constantz et al. |
| 2009/0289211 A1 | 11/2009 | Fujioka et al. |
| 2010/0132556 A1 | 6/2010 | Constantz et al. |
| 2010/0133120 A1 | 6/2010 | Varney et al. |
| 2010/0135865 A1 | 6/2010 | Constantz et al. |
| 2010/0137457 A1 | 6/2010 | Kaplan |
| 2010/0187123 A1 | 7/2010 | Bocarsly et al. |
| 2010/0193370 A1 | 8/2010 | Olah et al. |
| 2010/0276287 A1 | 11/2010 | Manoukian et al. |
| 2011/0114501 A1 | 5/2011 | Teamey et al. |
| 2011/0114502 A1 | 5/2011 | Cole et al. |
| 2011/0114503 A1 | 5/2011 | Sivasankar et al. |
| 2011/0114504 A1 | 5/2011 | Sivasankar et al. |
| 2011/0226632 A1 | 9/2011 | Cole et al. |
| 2011/0237830 A1 | 9/2011 | Masel |

FOREIGN PATENT DOCUMENTS

| | | |
|---|---|---|
| DE | 183856 C | 1/1906 |
| EP | 0012215 | 6/1980 |
| EP | 0293230 A | 11/1988 |
| EP | 0323300 A | 7/1989 |
| GB | 2230782 A | 10/1990 |
| JP | 201217300 | 1/2012 |
| WO | 2008110830 A | 9/2008 |
| WO | 2010007602 A | 1/2010 |
| WO | 2010063626 A | 6/2010 |
| WO | 2011120021 A | 9/2011 |
| WO | 2012006240 A | 1/2012 |
| WO | 2013006711 | 1/2013 |

OTHER PUBLICATIONS

Barrosse-Antle, L. et al., "Reduction of carbon dioxide in 1-butyl-3-methylimidazolium acetate", Chem. Commun. (2009), pp. 3744-3746.

Begum, A. et al., "Electrocatalysis of CO2 reduction by ruthenium benzothiazole and bithiazole complexes", Electrochemistry Communications 9 (2007), pp. 2525-2528.

Bell, A.T., "Basic Research Needs: Catalysis for Energy", U.S. Department of Energy Report PNNL-17214 (2008), p. 69.

Blizanac, B. et al., "Oxygen Reduction on Silver Low-Index Single-Crystal in Alkaline Solution: Rotating Ring DiskAg (hkl)", J. Phys. Chem. 110 (2006), pp. 4735-4741.

Bregoli, L., "The influence of platinum crystallite size on the electrochemical reduction of oxygen in phosphoric acid", Electrochimica Acta 23 (1978), pp. 489-492.

Cahill, L. et al., "Investigation of proton dynamics and the proton transport pathway in choline dihydrogen phosphate using solid-state NMR", Physical Chemistry Chemical Physics 12 (2010), pp. 5431-5438.

Chandrasekaran, K. et al., "In-situ spectroscopic investigation of adsorbed intermediate radicals in electrochemical reactions: carbon dioxide CO2—on platinum", Surface Science 185 (1987), pp. 495-514.

Chaplin, R. et al., "Effects of process conditions and electrode material on reaction pathways for carbon dioxide electroreduction with particular reference to formate formation", Journal of Applied Electrochemistry 33 (2003), pp. 1107-1123.

Chen, Q. et al., "Role of surface defect sites: From Pt model surfaces to shape-controlled nanoparticles", Chemical Science 3 (2012), pp. 136-147.

Cherstiouk, O. et al., "Model approach to evaluate particle size effects in electrocatalysis: Preparation and properties of Pt nanoparticles supported on GC and HOPG", Electrochimica Acta 48 (2003), pp. 3851-3860.

Cheung, K.C. et al., "Electrocatalytic reduction of carbon dioxide by a polymeric film of rhenium tricarbonyl dipyridylamine", Journal of Organometallic Chemistry 694 (2009), pp. 2842-2845.

Chu, D. et al., "Fixation of CO2 by electrocatalytic reduction and electropolymerization in ionic liquid-H2O solution", Chem. Sus. Chem. 1 (2008), pp. 205-209.

Cole, E. et al., "Using a one-electron shuttle for the multielectron reduction of CO2 to methanol: kinetic, mechanism, and structural insights", J. Am. Chem. Soc. 132 (2010), pp. 11539-11551.

Danly, D., "Development and commercialization of the Monsanto electrochemical adiponitrile process", J. Electrochemical Soc. 131 (1984), pp. 435C-442C.

Davis, Jr., J.H. et al., "Commercially available salts as building blocks for new ionic liquids", ACS Symp. Ser. 856 (2003), pp. 100-107.

Delacourt, C. et al., "Design of an electrochemical cell making syngas (CO + H2-) from CO2 and H2O reduction at room temperature", Journal of the Electrochemical Society 155 (2008), pp. B42-B49.

Delacourt, C. et al., "Mathematical modeling of a cation-exchange membrane containing two cations", Journal of the Electrochemical Society 155 (2008), pp. B1210-B1217.

Derien, S. et al., "Activation of carbon dioxide: nickel-catalyzed electrochemical carboxylation of diynes", J. Organic Chem. vol. 58. No. 9 (1993), pp. 2578-2588.

DeWulf, D.W. et al., "Electrochemical and surface studies of carbon dioxide reduction to methane and ethylene at copper electrodes in aqueous solutions", Journal of the Electrochemical Society 136 (1989), pp. 1686-1691.

DeWulf, D.W. et al., "The electrochemical reduction of CO2 to CH4 and C2H4 at Cu/Nafion electrodes (solid polymer electrolyte structures)", Catalysis Letters 1 (1988), pp. 73-80.

Dietz, H. et al., "Influence of substituted benzaldehydes and their derivatives as inhibitors for hydrogen evolution in lead/acid batteries", Journal of Power Sources 53 (1995), pp. 359-365.

Dube, P. et al., "Influence of adsorption processes on the CO2 electroreduction: An electrochemical mass spectrometry study", Journal of Electroanalytical Chemistry 582 (2005), pp. 230-240.

DuBois, D. in A. Bard, ed., "Encyclopedia of Electrochemistry", 7a, Springer (2006), pp. 202-225.

(56) References Cited

OTHER PUBLICATIONS

DuBois, D. et al., "Electrochemical reduction of carbon dioxide catalyzed by [Pd(triphosphine)(solvent)](BF4)2 complexes: synthetic and mechanistic studies", J. Am. Chem. Soc., vol. 113. No. 23 (1991), pp. 8753-8764.
Eggins, B.R. et al., "Improved yields of oxalate, glyoxylate and glycolate from the electrochemical reduction of carbon dioxide in methanol", Journal of Applied Electrochemistry 27 (1997), pp. 706-712.
Eggins, B.R. et al., "Voltammetry of carbon dioxide. Part 1. A general survey of voltammetry at different electrode materials in different solvents", J. Electroanalytical Chem. 148 (1983), pp. 17-24.
Fisher, B. et al., "Electrocatalytic reduction of carbon dioxide by using macrocycles of nickel and cobalt", J. Am. Chem. Soc., vol. 102, No. 24 (1980), pp. 7361-7363.
Franklin, T.C. et al., "The effect of quaternary ammonium salts on the anodic oxidation of ethanol", Surface Technology 24 (1985), pp. 143-155.
Fukuzumi, S., "Bioinspired Energy Conversion Systems for Hydrogen Production and Storage", Eur. J. Inorg. Chem., vol. 2008. No. 9. (2008), pp. 1351-1362.
Furuya, N. et al., "High performance Ru-Pd catalysts for CO2 reduction at gas-diffusion electrodes", Journal of Electroanalytical Chemistry 431 (1997), pp. 39-41.
Gattrell, M. et al. "A review of the aqueous electrochemical reduction of CO2 to hydrocarbons at copper", Journal of Electroanalytical Chemistry 594 (2006), pp. 1-19.
Gattrell, M. et al. "Electrochemical reduction of CO2 to hydrocarbons to store renewable electrical energy and upgrade biogas", Energy Conversion Management 48 (2007), pp. 1255-1265.
Haerens, K. et al., "Electrochemical decomposition of choline chloride based ionic liquid analogues", Green Chemistry 11 (2009), pp. 1357-1365.
Himeda, Y., "Conversion of CO2 into formate by homogeneously catalyzed hydrogenation in water: tuning catalytic activity and water solubility through the acid-base equilibrium of the ligand", European Journal of Inorganic Chemistry (2007), pp. 3927-3941.
Hori, Y. et al., "Electrochemical evidence of intermediate formation of adsorbed carbon monoxide in cathodic reduction of carbon dioxide at a nickel electrode", Electrochimica Acta 35 (1990), pp. 1777-1780.
Hori, Y. et al., "Electrochemical reduction of carbon dioxide at various series of copper single crystal electrodes", Journal of Molecular Catalysis A: Chemical 199 (2003), pp. 39-47.
Hori, Y., "Electrochemical CO2 reduction on metal electrodes", Modern Aspects of Electrochemistry 42 (2008), pp. 89-189.
Hoshi, N. et al., "Electrochemical reduction of carbon dioxide at a series of platinum single crystal electrodes", Electrochimica Acta 45 (2000), pp. 4263-4270.
Hoshi, N. et al., "Electrochemical reduction of carbon dioxide on kinked stepped surfaces of platinum inside the stereographic triangle", Journal of Electroanalytical Chemistry 540 (2003), pp. 105-110.
Hoshi, N. et al., "Electrochemical reduction of CO2 on single crystal electrodes of Ag(111), Ag(100), and Ag(110)", Journal of Electroanalytical Chemistry 440 (1997), pp. 283-286.
Ikeda, S. et al., "Electrochemical reduction of carbon dioxide using gas diffusion electrodes loaded with fine catalysts", Nanoscience and Nanotechnology (2008), pp. 108-113.
Ikeda, S. et al., "Zinc ion effect on electrochemical reduction of carbon dioxide at zinc electrode in aqueous solutions", Electrochemistry (Tokyo) 67 (1999), pp. 27-33.
Innocent, B. et al., "Electro-reduction of carbon dioxide to formate on lead electrode in aqueous medium", Journal of Applied Electrochemistry 39 (2009), pp. 227-232.
International Search Report and Written Opinion of the International Searching Authority issued on Oct. 31, 2011, in connection with PCT/US2011/042809.
International Search Report issued on Jul. 6, 2011, in connection with PCT/2011/030098.

Jiang, T. et al., "Solvent-free synthesis of substituted ureas from CO2 and amines with a functional ionic liquid as the catalyst", Green Chem. 10 (2008), pp. 465-469.
Jitaru, M., "Electrochemical carbon dioxide reduction—Fundamental applied topics (Review)", Journal of the University of Chemical Technology and Metallurgy 42 (2007), pp. 333-344.
Kabbabi, A. et al., "Particle size effect for oxygen reduction and methanol oxidation on Pt/C inside a proton exchange membrane", Journal of Electroanalytical Chemistry 373 (1994), pp. 251-254.
Third-Party Submissions Under 37 CFR 1.290, submitted on Sep. 17 and 18, 2013, in connection with co-owned U.S. Appl. No. 12/830,338, and Concise Description of Relevance for each of the references cited in the Third Party Submissions.
Tian, N. et al., "Direct electrodeposition of tetrahexahedral Pd nanocrystals with high-index facets and high catalytic activity for ethanol electrooxidation", Journal of the American Chemical Society 132 (2010), pp. 7580-7581.
Kaneco, S. et al. "Effect of sodium cation on the electrochemical reduction of CO2 at a copper electrode in methanol", Journal of Soild State Electrochemistry 11 (2007), pp. 490-495.
Kaneco, S. et al., "Carbon dioxide sequestration technology by electrochemical conversion at cadmium electrode in methanol under mild conditions", Photo/Electrochemistry & Photobiology in Environment, Energy and Fuel (2003), pp. 181-189.
Kaneco, S. et al., "Electrochemical reduction of carbon dioxide to ethylene at a copper electrode in methanol using potassium hydroxide and rubidium hydroxide supporting electrolytes", Electrochimica Acta 51 (2006), pp. 3316-3321.
Kaneco, S. et al., "Electrochemical reduction of carbon dioxide to ethylene with high Faradaic efficiency at a Cu electrode in CsOH/methanol", Electrochimica Acta 44 (1999), pp. 4701-4706.
Kaneco, S. et al., "Electrochemical reduction of CO2 in copper particle-suspended methanol", Chemical Engineering Journal 119 (2006), pp. 107-112.
Kaneco, S. et al., "Electrochemical reduction of CO2 to Methane at the Cu electrode in methanol with sodium supporting salts and its comparison with other alkaline salts", Energy & Fuels 20 (2006), pp. 409-414.
Kaneco, S. et al., "Photoelectrochemical reduction of CO2 at p-InP electrode in copper particle-suspended methanol", Chemical Engineering Journal 148 (2009), pp. 57-62.
Kinge, S. et al., "Dependence of CO oxidation on Pt nanoparticle shape: A shape-selective approach to the synthesis of PEMFC catalysts", Applied Organometallic Chemistry 22 (2008), pp. 49-54.
Kinoshita, K., "Particle size effects for oxygen reduction on highly dispersed platinum in acid electrolytes", Journal of the Electrochemical Society 137 (1990), pp. 845-848.
Koleli, F. et al., "Reduction of CO2 under high pressure and high temperature on Pb-granule electrodes in a fixed-bed reactor in aqueous medium", Applied Catalysis A—General 274 (2004), pp. 237-242.
Koper, M., "Structure sensitivity and nanoscale effects in electrocatalysis", Nanoscale 3 (2011), pp. 2054-2073.
Laitar, D.S. et al., "Efficient homogeneous catalysis in the reduction of CO2 to CO", Journal of the American Chemical Society 127 (2005), pp. 17196-17197.
Lee, C.W. et al., "Studies on suppression of hydrogen evolution reaction for zinc/air fuel cell", Material Science Forums 539-543 (2007), pp. 1427-1430.
Li, H. et al., "Development of a continuous reactor for the electro-reduction of carbon dioxide to formate—Part 1: Process variables", Journal of Applied Electrochemistry 36 (2006), pp. 1105-1115.
Li, H. et al., "Development of a continuous reactor for the electro-reduction of carbon dioxide to formate—Part 2: Scale-up", Journal of Applied Electrochemistry 37 (2007), pp. 1107-1117.
Li, W., "Electrocatalytic Reduction of CO2 to Small Organic Molecule Fuels on Metal Catalysts", Advances in CO2 Conversion and Utilization (2010), pp. 55-76.
Liu, Y. et al., "Observation of surface structural changes of Pt octahedron nanoparticles and its effect in electrocatalysis oxidation of methanol", Catalysis Communications 10 (2009), pp. 1244-1247.
Liu, Z. et al., "General rules for predicting where a catalytic reaction should occur on metal surfaces: A density functional theory study of

(56) References Cited

OTHER PUBLICATIONS

C-H and C-O bond breaking/making on flat, stepped, and kinked metal surfaces", Journal of the American Chemical Society 125 (2003), pp. 1958-1967.
Lopez-Cudero, A. et al., "CO electrooxidation on carbon supported platinum nanoparticles: Effect of aggregation", Journal of Electroanalytical Chemistry 644 (2010), pp. 117-126.
Lukaszewski, M. et al., "Electrosorption of carbon dioxide on platinum group metals and alloys—a review", Journal of Solid State Electrochemistry 13 (2009), pp. 813-827.
Lukaszewski, M. et al., "Comparative EQCM study on electrooxidation of carbon oxides adsorption products on noble metals and their alloys. Polycrystalline Pd-based systems", Journal of Electroanalytical Chemistry 606 (2007), pp. 117-133.
Ma, J. et al., "A short review of catalysis for CO2 conversion", Catal. Today 148 (2009), pp. 221-231.
Magdesieva, T.V. et al., "Lutetium monophthalocyanine and diphthalocyanine complexes and lithium naphthalocyanine as catalysts for electrochemical CO2 reduction", Journal of the Electrochemical Society 150 (2003), pp. E608-E612.
Maillard, F. et al., "Influence of particle agglomeration on the catalytic activity of carbon-supported Pt nanoparticles in CO monolayer oxidation", Physical Chemistry Chemical Physics 7 (2005), pp. 385-393.
Maillard, F. et al., "Size effects on reactivity of Pt nanoparticles in CO monolayer oxidation: The role of surface mobility", Faraday Discussions 125 (2004), pp. 357-377.
Masel, R., "Chemical Kinetics and Catalysis", Wiley (2001), pp. 702-742.
Meiwes-Broer, K., "Work functions of metal clusters", Hyperfine Interactions 89 (1994), pp. 263-269.
Morris, A. et al., "Electrocatalytic carbon dioxide activation: The rate-determining step of pyridinium-catalyzed CO2 reduction", Chem. Sus. Chem, 4 (2011), pp. 191-196.
Narayanan, R. et al., "Catalysis with transition metal nanoparticles in colloidal solution: Nanoparticle shape dependence and stability", Journal of Physical Chemistry B 109 (2005), pp. 12663-12676.
Noda, H. et al., "Electrochemical reduction of carbon dioxide at various metal electrodes in aqueous potassium hydrogen carbonate solution", Bull. Chem. Soc. Japan 63 (1990), pp. 2459-2462.
Ogura, K. et al., "CO2 attraction by specifically adsorbed anions and subsequent accelerated electrochemical reduction", Electrochimica Acta 56 (2010), pp. 381-386.
Ogura, K. et al., "Reduction of CO2 to ethylene at three-phase interface effects of electrode substrate and catalytic coating", Journal of the Electrochemical Society 152 (2005), pp. D213-D219.
Ogura, K. et al., "Selective formation of ethylene from CO2 by catalytic electrolysis at a three-phase interface", Prepr. Pap.—Am. Chem. Soc., Div. Fuel Chem. 49 (2004), pp. 9-10.
Ohya, S. et al., "Electrochemical reduction of CO2 in methanol with aid of CuO and Cu2O", Catalysis Today 148 (2009), pp. 329-334.
Oloman, C. et al., "Electrochemical processing of carbon dioxide", Chem. Sus. Chem. 1 (2008), pp. 385-391.
O'Mahony, A.M. et al., "The electrochemical reduction of hydrogen sulfide on platinum in several room temperature ionic liquids", The Journal of Physical Chemistry C112 (2008), pp. 7725-7730.
Pease, R.N. et al., "The catalytic combination of ethylene and hydrogen in the presence of metallic copper. III. Carbon monoxide as a catalyst poison", J. Am. Chem. Soc. 47 (1925), pp. 1235-1240.
Perez, E.R. et al., "In situ FT-IR and ex situ EPR analysis for the study of the electroreduction of carbon dioxide in N,N-dimethylformamide on a gold interface", Journal of Electroanalytical Chemistry 578 (2005), pp. 87-94.
Perez, J. et al., "Particle size effect for ethanol electro-oxidation on Pt/C catalysts in half-cell and in a single direct ethanol fuel cell", Journal of Electroanalytical Chemistry 654 (2011), pp. 108-115.
Photinon, K. et al., "Thick-Film carbon dioxide sensor via anodic adsorbate stripping technique and its structural dependence", Sensors 9 (2009), pp. 7203-7216.

Podlovchenko, B.I. et al., "Electroreduction of carbon dioxide on palladium electrodes at potentials higher than the reversible hydrogen potential", Journal of Electroanalytical Chemistry 373 (1994), pp. 185-187.
Popic, J.P. et al., "Reduction of carbon dioxide on ruthenium oxide and modified ruthenium oxide electrodes in 0.5 M NaHCO3", Journal of Electroanalytical Chemistry 421 (1997), pp. 105-110.
Qu, J. P. et al., "Electrochemical reduction of CO2 on RuO2/TiO2 nanotubes composite modified Pt electrode", Electrochimica Acta 50 (2005), pp. 3576-3580.
Raebiger, J.W. et al., "Electrochemical Reduction of CO2 to CO Catalyzed by a Bimetallic Palladium Complex", Organometallics 25 (2006), pp. 3345-3351.
Rakowski, M. et al., "Development of molecular electrocatalysts for CO2 reduction and H2 production/oxidation", Acc. Chem. Res. 42 (2009), pp. 1974-1982.
Ramirez, G. M. et al., "A supramolecular cobalt-porphyrin-modified electrode, toward the electroreduction of CO2", Journal of Coordination Chemistry 57 (2004), pp. 249-255.
Rezaei, B. et al., "Application of ionic liquids as an electrolyte additive on the electrochemical behavior of lead acid battery", Journal of Power Sources 187 (2009), pp. 605-612.
Rezaei, B. et al., "Effects of tetrabutylammonium hydrogen sulfate as an electrolyte additive on the electrochemical behavior of lead acid battery", Journal of Solid State Electrochemistry 12 (2008), pp. 1663-1671.
Rodriguez, P. et al., "Specific surface reactions for identification of platinum surface domains: Surface characterization and electrocatalytic tests", Electrochimica Acta 50 (2005), pp. 4308-4317.
Rosen, B. et al., "Ionic Liquid-Mediated Selective Conversion of CO2 to CO at Low Overpotentials", Science 334 (2011), pp. 643-644.
Urey, H. et al., "Some reactions of atomic hydrogen", Journal of the American Chem. Society 51 (1929), pp. 3286-3290.
Weiss, A. et al., "Formose sugars from formaldehyde", Applied Catalysis 1 (1981), pp. 237-246.
Idriss, H. et al., "Two routes to formaldehyde from formic acid on TiO2, (001) surfaces", Surface Science 348 (1996), pp. 39-48.
Kiss, G. et al., "Palladium-catalyzed reppe carbonylation", Chem. Rev. 101 (2001), pp. 3435-3456.
Jessop, P. et al., "Recent advances in the homogeneous hydrogenation of carbon dioxide", Coordination Chem. Rev. 248 (2004), pp. 2425-2442.
Gazsi, A. et al., "Decomposition and reforming of formic acid on supported Au catalysts: Production of CO-free H2", Journal of Physical Chem. C 115 (2011), pp. 15459-15466.
Sabatier, P. et al., "Chimie Organique.—Sur la decomposition catalytique de l 'acide formique", Comptes Rendus Hebdomadaires Des Seances De L'Academie Dessciences 152 (2011), pp. 1213-1215.
Deng, J. et al., "Linked strategy for the production of fuels via formose reaction", Scientific Reports 3 (2013), p. 1244.
International Search Report and Written Opinion issued on Jun. 17, 2014 in connection with PCT/US2014/018067.
D. Dubois, "Electrochemical Reactions of Carbon Dioxide", Encyclopedia of Electrochemistry, pp. 212 (2007).
International Search Report and Written Opinion issued on May 16, 2014 in connection with PCT/US2013/061506.
Saeki, T. et al., "Electrochemical reduction of CO2 with high current density in a CO2 + methanol medium at various metal electrodes", Journal of Electroanalytical Chemistry 404 (1996), pp. 299-302.
Saeki, T. et al., "Electrochemical reduction of liquid CO2. Drastic enhancement of current density", Journal of the Electrochemical Society 141 (1994), pp. L130-L132.
Scheijen, F. et al., "The electrooxidation of small organic molecules on platinum nanoparticles supported on gold: Influence of platinum deposition procedure", Journal of Solid State Electrochemistry 12 (2008), pp. 483-495.
Seshadri, G. et al., "A new homogeneous electrocatalyst for the reduction of carbon dioxide to methanol at low overpotential", J. Electroanalytical Chemistry 372 (1994), pp. 145-150.

(56) References Cited

OTHER PUBLICATIONS

Silvester, D.S. et al., "Electrochemical reduction of benzoic acid and substituted benzoic acids in some room temperature ionic liquids", The Journal of Physical Chemistry C112 (2008), pp. 12966-12973.
Silvester, D.S. et al., "Electrochemistry in room temperature ionic liquids: A review and some possible applications", Z. Phys. Chem. 220 (2006), pp. 1247-1274.
Singh, P. et al., "Comparison of Oxygen Reduction Reaction at Silver Nanoparticles and Polycrystalline Silver Electrodes in Alkaline Solution", J. Phys. Chem. 116 (2012), pp. 10656-10663.
Smolinka, T. et al., "$CO_2$ reduction on Pt electrocatalysts and its impact on $H_2$ oxidation in $CO_2$ containing fuel cell feed gas—A combined in situ infrared spectroscopy, mass spectrometry and fuel cell performance study", Electrochimica Acta 50 (2005), pp. 5189-5199.
Smolinski, S. et al., "Effect of surface order on adsorption of sulfate ions on silver electrodes", Journal of Electroanalytical Chemistry 442 (1998), pp. 41-47.
Sobkowski, J. et al., "Interaction of sulfate ions with monocrystalline silver electrodes", Colloids Surfaces A: Physicochem. Eng. Aspects 134 (1998), pp. 39-45.
Solla-Gullon, J. et al., "CO monolayer oxidation on semi-spherical and preferentially oriented (1 0 0) and (1 1 1) platinum nanoparticles", Electrochemistry Communications 8 (2006), pp. 189-194.
Solla-Gullon, J. et al., "Shape dependent electrocatalysis", Annual Reports on the Progress of Chemistry—Section C 107 (2011), pp. 263-297.
Solla-Gullon, J. et al., "Shape-dependent electrocatalysis: Methanol and formic acid electrooxidation on preferentially oriented Pt nanoparticles", Physical Chemistry Chemical Physics 10 (2008), pp. 3689-3698.
Star, A. et al., "Nanoelectric carbon dioxide sensors", Advanced Materials 16 (2004), pp. 2049-2051.
Subramanian, K. et al., "Electrochemical membrane reactor for the reduction of carbon dioxide to formate", Journal of Applied Electrochemistry 37 (2007), pp. 255-260.
Sun, J. et al., "Hydroxyl-functionalized ionic liquid: a novel efficient catalyst for chemical fixation of $CO_2$ to cyclic carbonate", Tetrahedron Letters 49 (2008), pp. 3588-3591.
Sung, Y.-E. et al., "Structure of chemisorbed sulfur on a Pt(III) electrode", Journal of the American Chemical Society 119 (1997), pp. 194-200.
Takahashi, I. et al., "Electrochemical reduction of $CO_2$ at copper single crystal Cu(S)-[n(111) Ã—(111)] and Cu(S)-[n (110) Ã—(100)] electrodes", Journal of Electroanalytical Chemistry 533 (2002), pp. 135-143.
Tian, N. et al., "Platinum metal catalysts of high-index surfaces: from single-crystal planes to electrochemically shape-controlled nanoparticles", Journal of Physical Chemistry C112 (2008), pp. 19801-19817.
Tian, N. et al., "Synthesis of tetrahexahedral platinum nanocrystals with high-index facets and high electro-oxidation activity", Science 316 (2007), pp. 732-735.
Udupa, K.S. et al., "Electrolytic reduction of carbon dioxide to formic acid", Electrochimica Acta 16 (1971), pp. 1593-1598.
Welton, T., "Room-Temperature Ionic Liquids. Solvents for Synthesis and Catalysis". Chem. Revs., vol. 99, No. 8 (1999), pp. 2071-2083.
Wong, W.L. et al., "A robust ionic liquid as reaction medium and efficient organocatalyst for carbon dioxide fixation", Chem. Sus. Chem. 1 (2008), pp. 67-70.
Written Opinion of the International Searching Authority issued on Sep. 26, 2012, in connection with PCT/US2011/030098.
Xu, X. et al., "Effects of imidazolium salts as cocatalysts on the copolymerization of $CO_2$ with epoxides catalyzed by (salen)CrIIICI complex", Polymer 48 (2007), pp. 3921-3924.
Yan, T. et al., "Adsorption of $CO_2$ on the rutile (110) surface in ionic liquid. A molecular dynamics simulation", J. Phys. Chem. C 113 (2009), pp. 19389-19392.

Yang, H. et al., "Electrochemical activation of carbon dioxide in ionic liquid: synthesis of cyclic carbonates at mild reaction conditions", Chem. Commun. (2002), pp. 274-275.
Yano, H. et al., "Particle-size effect of nanoscale platinum catalysts in oxygen reduction reaction: An electrochemical and 195Pt EC-NMR study", Physical Chemistry Chemical Physics 8, 4932-4939 (2006).
Yano, H. et al., "Selective electrochemical reduction of $CO_2$ to ethylene at a three-phase interface on copper(I) halide-confined Cu-mesh electrodes in acidic solutions of potassium halides", Journal of Electroanalytical Chemistry 565 (2004), pp. 287-293.
Yano, J. et al., "Selective ethylene formation by pulse-mode electrochemical reduction of carbon dioxide using copper and copper-oxide electrodes", Journal of Solid State Electrochemistry 11 (2006), pp. 554-557.
Yano, M. et al., "Effects of additives in zinc alloy powder on suppressing hydrogen evolution", Journal of Power Sources 74 (1998), pp. 129-134.
Yoshizawa-Fujita, M. et al., "A new class of proton-conducting ionic plastic crystals based on organic cations and dihydrogen phosphate", Electrochemistry Communications 9 (2007), pp. 1202-1205.
Yu, D. et al., "Carboxylation of Terminal Alkynes with Carbon Dioxide Catalyzed by Poly(N-Heterocyclic Carbene)-Supported Silver Nanoparticles", Adv. Synth. Catal. 354 (2012), pp. 969-974.
Yuan, D. et al., "Electrochemical activation of carbon dioxide for synthesis of dimethyl carbonate in an ionic liquid", Electrochimica Acta 54 (2009), pp. 2912-2915.
Zhang, L. et al., "Electrochemical activation of $CO_2$ in ionic liquid (BMIMBF4): synthesis of organic carbonates under mild conditions", Green Chemistry 10 (2008), pp. 202-206.
Zhang, S. et al., "Chiral ionic liquids improved the asymmetric cycloaddition of $CO_2$ to epoxides", Green Chem. 11 (2009), pp. 935-938.
Zhang, Z. et al., "Hydrogenation of carbon dioxide is promoted by a task-specific ionic liquid", Angew. Chem. Int. Ed. 47 (2008), pp. 1127-1129.
Zhang, Z. et al., "Hydrogenation of $CO_2$ to formic acid promoted by a diamine-functionalized ionic liquid", Chem. Sus. Chem. 2 (2009), pp. 234-238.
Zhao, G. et al., "Electrochemical reduction of supercritical carbon dioxide in ionic liquid 1-n-butyl-3-methylimidazolium hexafluorophosphate", Journal of Supercritical Fluids 32 (2004), pp. 287-291.
Zhou, W. et al., "Size effects in electronic and catalytic properties of unsupported palladium nanoparticles in electrooxidation of formic acid", Journal of Physical Chemistry B 110 (2006), pp. 13393-13398.
Zhu, A., "Supported cholinechloride/urea as a heterogeneous catalyst for chemical fixation of carbon dioxide to cyclic carbonates", Green Chemistry. vol. 9 (2007), pp. 169-172.
International Search Report and Written Opinion issued on Feb. 15, 2013 in connection with PCT/US2012/043651.
Ikeda, S. et al., "Selective Formation of Formic Acid. Oxalic Add, and Carbon Monoxide by Electrochemical Reduction of Carbon Dioxide", Bull. Chem. Soc. Japan, vol. 60, (1987), pp. 2517-2522.
International Preliminary Report on Patentability issued on Jan. 3, 2013 in connection with International Application No. PCT/US2011/030098521.
Kaneco, S. et al., "Electrochemical conversion of carbon dioxide to formic acid on Pb in KOH/methane electrolyte at ambient temperature and pressure", Energy, vol. 23, No. 12 (1998), pp. 1107-1112.
Ogura, K. et al., "Selective formation of ethylene from $CO_2$ by catalytic electrolysis at a three—phase interface", Catalysis Today 98 (2004), pp. 515-521.
Scibioh, M. et al., "Electrochemical Reduction of Carbon Dioxide: A Status Report", Indian Natn. Sci. Acad., vol. 70, A, No. 3, (2004), pp. 407-462.
International Preliminary Report on Patentability issued on Jan. 9, 2014 in connection with International Application PCT/US2012/043651.

\* cited by examiner

HYDROGENATION OF FORMIC ACID TO FORMALDEHYDE

CROSS-REFERENCE TO RELATED APPLICATIONS

This application is related to U.S. Non-Provisional patent application Ser. No. 12/830,338, filed on Jul. 4, 2010, and to corresponding International Application No. PCT/US2011/030098, filed on Mar. 25, 2011, both entitled "Novel Catalyst Mixtures". The '338 non-provisional and '098 international applications both claimed priority benefits from U.S. Provisional Patent Application Ser. No. 61/317,955 filed on Mar. 26, 2010, entitled "Novel Catalyst Mixtures". This application is also related to U.S. Non-Provisional patent application Ser. No. 13/626,873, filed on Sep. 25, 2012, which claimed priority benefits and continuation status from the '098 international application.

This application is also related to U.S. Non-Provisional patent application Ser. No. 13/174,365, filed Jun. 30, 2011, and to International Application No. PCT/US2011/042809, filed on Jul. 1, 2011, both entitled "Novel Catalyst Mixtures". The '365 non-provisional application claimed priority benefits from U.S. Provisional Patent Application Ser. No. 61/484,072, filed on May 9, 2011, entitled "Novel Catalyst Mixtures". The '809 international application claimed priority benefits from the '338 non-provisional, the '098 international, the '072 provisional, and the '365 non-provisional applications.

The present application is also related to U.S. Non-Provisional patent application Ser. No. 13/530,058, filed on Jun. 21, 2012, entitled "Sensors For Carbon Dioxide And Other End Uses", and corresponding International Patent Application No. PCT/US2012/043651, filed on Jun. 22, 2012, entitled "Low Cost Carbon Dioxide Sensors". The '058 non-provisional and '651 international applications both claimed priority benefits from U.S. Provisional Patent Application Ser. No. 61/499,225, filed on Jun. 21, 2011, entitled "Low Cost Carbon Dioxide Sensors".

This application is also related to U.S. Non-Provisional patent application Ser. No. 13/445,887, filed on Apr. 12, 2012, "Electrocatalysts For Carbon Dioxide Conversion". The '887 nonprovisional application claimed priority benefits from U.S. Provisional Application 61/499,225, filed on Jun. 21, 2011, entitled "Low Cost Carbon Dioxide Sensors", and from U.S. Provisional Patent Application Ser. No. 61/540,044, filed on Sep. 28, 2011, entitled "On Demand Carbon Monoxide Generator for Therapeutic and Other Applications". The '887 non-provisional application also claimed priority benefits and continuation-in-part status from the '338 non-provisional application.

Each of the above applications is hereby incorporated by reference herein in its entirety.

FIELD OF THE INVENTION

The present invention relates to catalytic chemistry and in particular to processes for catalytically converting carbon dioxide to useful fuels or chemicals, including formaldehyde, acrylic acid, ethane, propane, ethylene, propylene, butene, and carbohydrates comprising at least 5 carbon atoms.

BACKGROUND OF THE INVENTION

Recycling generated carbon dioxide back to fuels and chemicals would make a tremendous difference to the U.S. economy. Presently, fuels and organic chemicals are usually made from petroleum, coal, and/or natural gas "fossil fuels." However, if such fuels and chemicals could be made from $CO_2$, then the U.S. dependence on imported oil would be lessened, and emissions of greenhouse gases that are thought to contribute to global warming would be reduced. $CO_2$ produced in power plants would change from a waste product to a useful, economically viable feedstock. Solar and wind energy could also be stored in the form of hydrocarbon fuels.

Presently, however, most large volume organic chemicals are made from fossil fuels. For example, most acrylic acid produced in the U.S. is currently made from propylene. The propylene is made from petroleum. Most formaldehyde now produced in the U.S. is manufactured by oxidation of methanol. The methanol is manufactured from natural gas or coal. Ethylene is made by cracking of light olefins from petroleum, or from methanol. If these products could be made from $CO_2$, the use of fossil fuels in the U.S. would be reduced, as would the emissions of greenhouse gases.

U.S. Pat. No. 8,212,088 describes an environmentally beneficial process for preparing a fuel or chemical, in which carbon dioxide from a natural source, or carbon dioxide from an artificial chemical source that would otherwise be discharged into the environment by the artificial chemical source, is converted to useful fuels and chemicals. In the process described in the '088 patent, $CO_2$ is first converted to a mixture of formic acid and other compounds. The formic acid is then sent to a second process where it undergoes a 4-electron hydrogenation to form methanol. The methanol is then converted to fuels and chemicals using conventional chemical processes, as illustrated in FIG. 1. The advantage of converting $CO_2$ to methanol is that infrastructure already exists to convert methanol into other products.

The limitation in the process described in the '088 patent is that the hydrogenation to methanol is an extra step in the conversion process that wastes energy, and that may not be needed at all. For example, almost half of the methanol produced worldwide is further reacted to yield formaldehyde via an oxidative dehydrogenation process. Energy is wasted when formic acid is first hydrogenated to methanol and then dehydrogenated to formaldehyde, as illustrated in FIG. 2A. Moreover, the intermediate methanol can be a safety hazard, because it is highly flammable and the flame is invisible.

As described in more detail below, the present environmentally beneficial process for the production of fuels and chemicals preferably employs carbon dioxide from a natural source or carbon dioxide from an artificial chemical source that would otherwise be discharged into the environment by the artificial chemical source. The carbon dioxide is converted to formic acid and other products. The formic acid is then converted to fuels and/or chemicals without the intermediate process of hydrogenating the formic acid to methanol or reacting the formic acid with ammonia to form formamide.

By contrast, the '088 patent describes a method in which (a) carbon dioxide is converted to formic acid and other products, (b) the formic acid is hydrogenated to form methanol, and then (c) the methanol is converted to fuels and chemicals. For example, FIGS. 2A and 2B compare the process for the formation of formaldehyde disclosed in the '088 patent (FIG. 2A) and that disclosed in the present application (FIG. 2B). As shown, the process disclosed in the present application uses half as much hydrogen as the process described in the '088 patent, and does not require temperatures as high as those used in the process described in the '088 patent.

In the process disclosed herein, only a small fraction (namely, less than 10%) of the formic acid is hydrogenated to methanol. In the present process, formic acid can be made by any method, and the formic acid is then converted to fuels and chemicals without the intermediate process of hydrogenating the formic acid to methanol or reacting it with ammonia to form formamide. The present process produces fuels and chemicals in which formic acid is converted to one of seven primary feedstocks: formaldehyde, acrylic acid, methane, ethylene, propylene, syngas, and C5-C7 carbohydrates, without the intermediate process of hydrogenating the formic acid to methanol or reacting it with ammonia to form formamide. The formaldehyde, acrylic acid, methane, ethylene, propylene, syngas and/or short chain carbohydrates can either be used directly, or can be converted into a wealth of other products, as illustrated in FIG. 3. The list of products in FIG. 3 is not meant to limit the present process. Rather, it provides examples of products that can be made from formic acid following the teachings of this application.

In the present process for the production of formaldehyde, and products made using formaldehyde, formic acid is converted to formaldehyde without a separate intermediate process of hydrogenating the formic acid to methanol. The present process encompasses processes in which hydrogen reacts with formic acid to form formaldehyde. The process can occur in the presence of a catalyst comprising an oxide of at least one of the following elements: Mg, Ca, Sr, Ba, Ti, Y, Lu, Ti, Zr, Hf, V, Nb, Ta, Cr, Mo, W, Fe, Co, Ni, Cu, Zn, Al, Ga, In, Tl, Si, Ge, Sn, Sb, Bi, Se, Te, Pb, La, Ce, Pr, Th, Nd, Pm, U, Sm, Eu, Gd, Tb, Dy, Ho, Er, Tm, or Yb, preferably the oxides of cerium or tellurium. Reaction temperature can be between 8° C. and 350° C., preferably between 40° C. and 200° C., most preferably between 60° C. and 100° C.

The present process also produces organic acids with at least three carbon atoms specifically including acrylic acid, methyl acrylic acid or propionic acid, wherein formic acid directly or indirectly reacts with an unsaturated hydrocarbon to yield the organic acid. The present process encompasses systems for produce the organic acids from formic acid and an unsaturated hydrocarbon comprising at least two reactors in series, in which the temperature of each reactor can be controlled independently. The present process also encompasses systems with one reactor containing an acid catalyst and a second reactor containing a catalyst comprising at least one of a nickel salt, a copper salt and a palladium salt.

The present process also produces olefins such as ethylene and propylene and products synthesized from olefins, in which formic acid is converted to the olefins ethylene and/or propylene without a separate intermediate process of hydrogenating the formic acid to methanol. In the present process, formic acid is first converted to formaldehyde as described above and the formaldehyde is then further converted to olefins such as ethylene, propylene or butylene. The process can employ a base catalyst to condense the formaldehyde into a multi-carbon species, followed by an acid catalyst to convert the multi-carbon species into olefins. The acid catalyst can be in the form of a zeolite such as ZMS-5 or SAPO-43. The present process encompasses the use of CO2 to modify the pH of the mixture after some of the formaldehyde has been condensed. In some embodiments, the present process employs ZSM-5 or SAPO-43 in the conversion of formic acid to a product comprising propylene. ZSM-5 is an aluminosilicate zeolite mineral belonging to the pentasil family of zeolites, having the chemical formula is $Na_nAl_nSi_{96-n}O_{192}.16H_2O$ ($0 < n < 27$); it is widely used in the petroleum industry as a heterogeneous catalyst for hydrocarbon isomerization reactions (see http://en.wikipedia.org/wiki/ZSM-5, downloaded on Feb. 23, 2013). SAPO-43 is a small pore silico-alumino-phosphate (see http://pubs.acs.org/doi/abs/10.1021/1a026424j, downloaded on Feb. 23, 2013).

The present process also produces carbohydrates or molecules produced from carbohydrates, in which formic acid is converted to a carbohydrate without a separate intermediate process of hydrogenating the formic acid to methanol. In the present process, the formic acid is converted to formaldehyde as described above, and the formaldehyde is then reacted in the presence of a base catalyst to yield a carbohydrate. Calcium hydroxide is a preferred catalyst in the present process, and the present process specifically encompasses the use of carbon dioxide for the removal of calcium from solution.

The present process also produces syngas or molecules produced from syngas, in which formic acid is converted to syngas without a separate intermediate process of hydrogenating the formic acid to methanol. The present process preferably employs two parallel reactors to convert the formic acid into syngas, wherein the temperatures of the two independent reactors can be independently controlled. It is preferred that one of the reactors contains an acid catalyst while the other reactor preferably contains a metallic catalyst.

SUMMARY OF THE INVENTION

Shortcomings and limitations of existing processes for converting $CO_2$ to useful fuels or chemicals are overcome by a process for the production of fuels and chemicals comprising the steps of forming an amount of formic acid and non-biologically converting the amount of formic acid to a product comprising an organic intermediate. Less than 10% of the amount of formic acid is hydrogenated to methanol or reacted with ammonia to form formamide.

In a preferred embodiment, the process further comprises initially converting an amount of carbon dioxide obtained from a natural source or from an artificial chemical source to produce the amount of formic acid, thereby reducing the amount of carbon dioxide present in nature or diverting the amount of carbon dioxide from being discharged into the environment by the artificial chemical source.

The formic acid is preferably converted to a product comprising at least one of formaldehyde, acrylic acid, ethane, propane, ethylene, propylene, butene, and a carbohydrate comprising at least five carbon atoms. In a preferred process, the formic acid is hydrogenated to form a product comprising formaldehyde.

In a preferred embodiment, the process further comprises reacting the formic acid with hydrogen in the presence of a catalyst comprising oxygen and at least one of Mg, Ca, Sr, Ba, Ti, Y, Lu, Ti, Zr, Hf, V, Nb, Ta, Cr, Mo, W, Fe, Co, Ni, Cu, Zn, Al, Ga, In, Tl, Si, Ge, Sn, Sb, Bi, Se, Te, Pb, La, Ce, Pr, Th, Nd, Pm, U, Sm, Eu, Gd, Tb, Dy, Ho, Er, Tm, and Yb. The catalyst is preferably a metal oxide comprising at least one of cerium (IV) oxide and tellurium (IV) oxide. In a preferred process, reaction temperature is between 8° C. and 300° C.

In a preferred embodiment, the process further comprises a formose step in which the formaldehyde is converted to formose sugars. The formose step preferably comprises reacting the formaldehyde in the presence of $Ca(OH)_2$ to produce C5 and C6 sugars. The process can further comprise a hydrocarbon step in which the formose sugars are converted to a product comprising at least one of paraffin and olefins. The hydrocarbon step preferably converts the formose sugars to a product comprising at least one of ethane, propane, ethylene, propylene and butene. The hydrocarbon step preferably employs a catalyst comprising a zeolite, more preferably a silico-alumino-phosphate zeolite or an aluminosilicate zeolite.

In a preferred embodiment, the process further comprises an acid-converting step in which the amount of formic acid is converted to an organic acid comprising at least 3 carbon atoms. The organic acid is preferably at least one of acrylic acid and methylacrylic acid.

In a preferred embodiment, the process further comprises converting the formic acid to a product comprising at least one of carbon monoxide and hydrogen. The product comprising both of carbon monoxide and hydrogen is preferably produced by reacting the formic acid in at least two parallel reactors having temperatures independently controllable. One of the reactors preferably contains a metallic catalyst capable of yielding hydrogen. The other reactor preferably contains a catalyst comprising at least one of an oxide, an acid and a base to yield carbon monoxide. The hydrogen and carbon monoxide are mixed to yield syngas.

A process for the production of formaldehyde comprises hydrogenating an amount of formic acid to form a product comprising formaldehyde, in which the formaldehyde is formed without hydrogenating more than 10% of the amount of formic acid to methanol. The process preferably further comprises initially converting an amount of carbon dioxide obtained from a natural source or from an artificial chemical source to produce the amount of formic acid, thereby reducing the amount of carbon dioxide present in nature or diverting the amount of carbon dioxide from being discharged into the environment by the artificial chemical source.

In a preferred embodiment, the process for the production of formaldehyde further comprises reacting the formic acid with hydrogen in the presence of a catalyst comprising oxygen and at least one of Mg, Ca, Sr, Ba, Ti, Y, Lu, Ti, Zr, Hf, V, Nb, Ta, Cr, Mo, W, Fe, Co, Ni, Cu, Zn, Al, Ga, In, Tl, Si, Ge, Sn, Sb, Bi, Se, Te, Pb, La, Ce, Pr, Th, Nd, Pm, U, Sm, Eu, Gd, Tb, Dy, Ho, Er, Tm, and Yb. The preferred catalyst is a metal oxide comprising at least one of cerium (IV) oxide and tellurium (IV) oxide. The preferred reaction temperature is between 8° C. and 350° C., more preferably between 40° C. and 200° C., and even more preferably between 60° C. and 100° C.

A process for the production of an organic acid having at least three carbon atoms comprises the steps of forming an amount of formic acid and reacting the amount of formic acid with an amount of an unsaturated hydrocarbon.

In a preferred embodiment of the process for the production of an organic acid, the unsaturated hydrocarbon is preferably one of acetylene and methylacetylene, and the organic acid is preferably one of acrylic acid and methyl acrylic acid. The reacting step is preferably performed in the presence of a mixture comprising a phosphine ligand, a strong acid and a catalyst comprising at least one of a palladium salt, a copper salt and a nickel salt. Reaction temperature is preferably between 50° C. and 350° C. The formic acid preferably contacts an acid catalyst before being introduced into a vessel containing the mixture. The acid catalyst temperature is preferably different than the mixture temperature, with the preferred acid catalyst temperature being at least 100° C., more preferably at least 130° C.

A process for the production of at least one of a C5 sugar and a C6 sugar comprises the steps of forming an amount of formic acid, non-biologically converting the amount of formic acid to a product comprising an organic intermediate, in which less than 10% of the amount of formic acid is hydrogenated to form a product comprising formaldehyde, and reacting the product comprising formaldehyde over a base catalyst to yield a solution comprising at least one of a C5 sugar and a C6 sugar.

In a preferred embodiment of the process for the production of at least one of a C5 sugar and a C6 sugar, reaction temperature is between 50° C. and 70° C. The base catalyst preferably comprises $Ca(OH)_2$. The process preferably further comprises removing calcium from the sugar solution by bubbling a gas comprising carbon dioxide through the sugar solution to produce a sugar solution substantially free of calcium. The sugar solution substantially free of calcium preferably has a pH value between 4 and 7.

A process for the production of olefins comprises the steps of forming an amount of formic acid and non-biologically converting the amount of formic acid to a product comprising an organic intermediate in which less than 10% of the amount of formic acid is hydrogenated to form a product comprising formaldehyde, reacting the product comprising formaldehyde over a base catalyst comprising $Ca(OH)_2$ to yield a solution comprising at least one of a C5 sugar and a C6 sugar, removing calcium from the sugar solution by bubbling a gas comprising carbon dioxide through the sugar solution to produce a sugar solution substantially free of calcium, and reacting the sugars in the presence of an acid catalyst to form a product comprising at least one olefin. The preferred acid catalyst comprises a zeolite, more preferably a silico-alumino-phosphate zeolite.

A process for the production of propylene comprises the steps of forming an amount of formic acid; and non-biologically converting the amount of formic acid to a product comprising an organic intermediate, wherein less than 10% of the amount of formic acid is hydrogenated to form a product comprising formaldehyde, reacting the product comprising formaldehyde over a base catalyst comprising $Ca(OH)_2$ to yield a solution comprising at least one of a C5 sugar and a C6 sugar, removing calcium from the sugar solution by bubbling a gas comprising carbon dioxide through the sugar solution to produce a sugar solution substantially free of calcium, and reacting the sugars in the presence of an aluminosilicate zeolite catalyst to form a product comprising propylene.

DETAILED DESCRIPTION OF PREFERRED EMBODIMENT(S)

Figure 1:
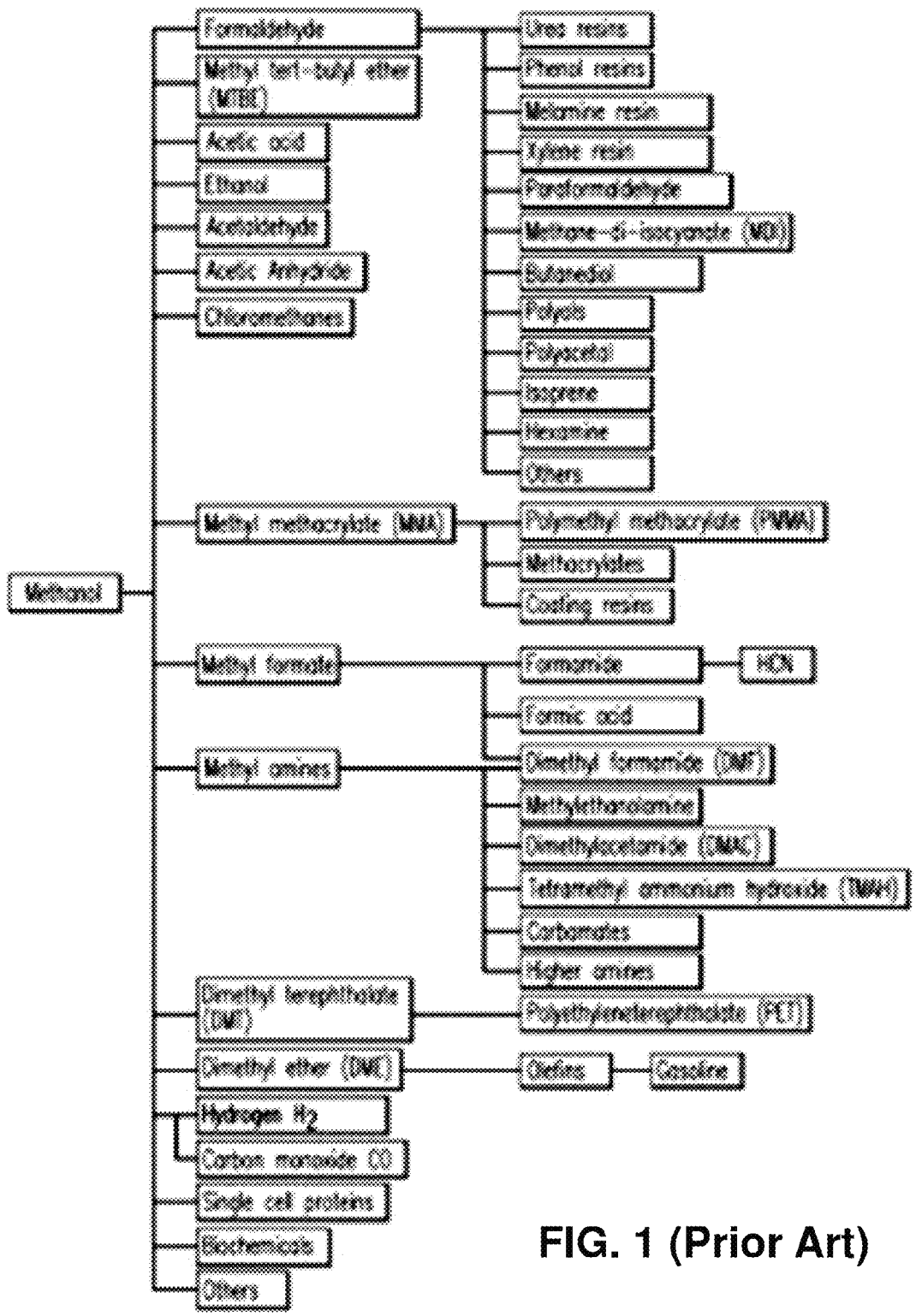
FIG. 1 (Prior Art) is a schematic diagram of products that can be produced from methanol, as described in the '088 patent.
Figure 2A:
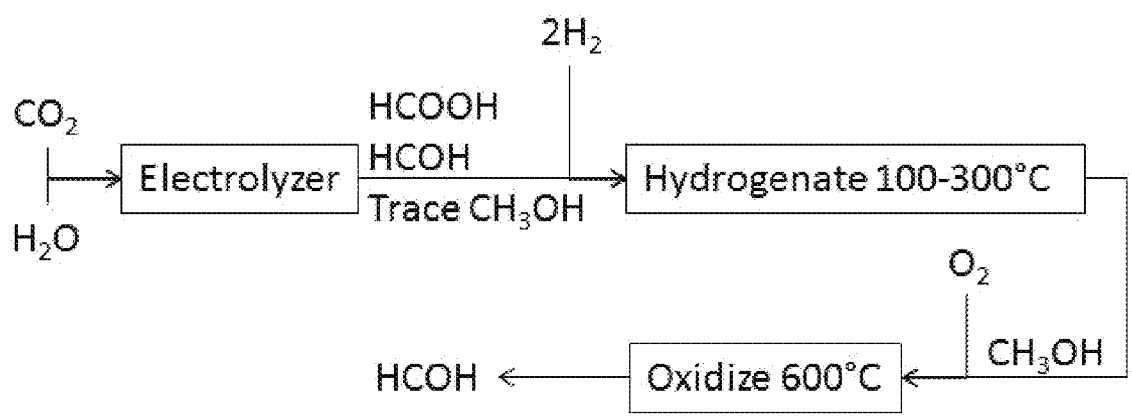
FIG. 2 is a schematic diagram comparing (A) the process for formaldehyde production as described in the '088 patent to (B) the process for formaldehyde production as disclosed in the present application.
Figure 2B:
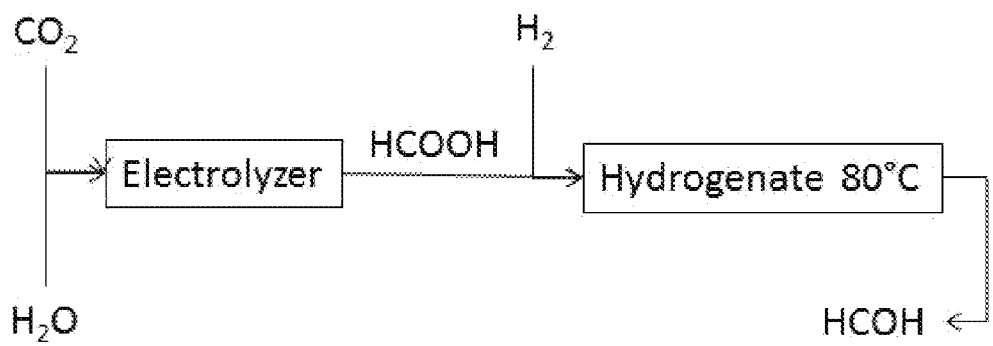
Figure 3:
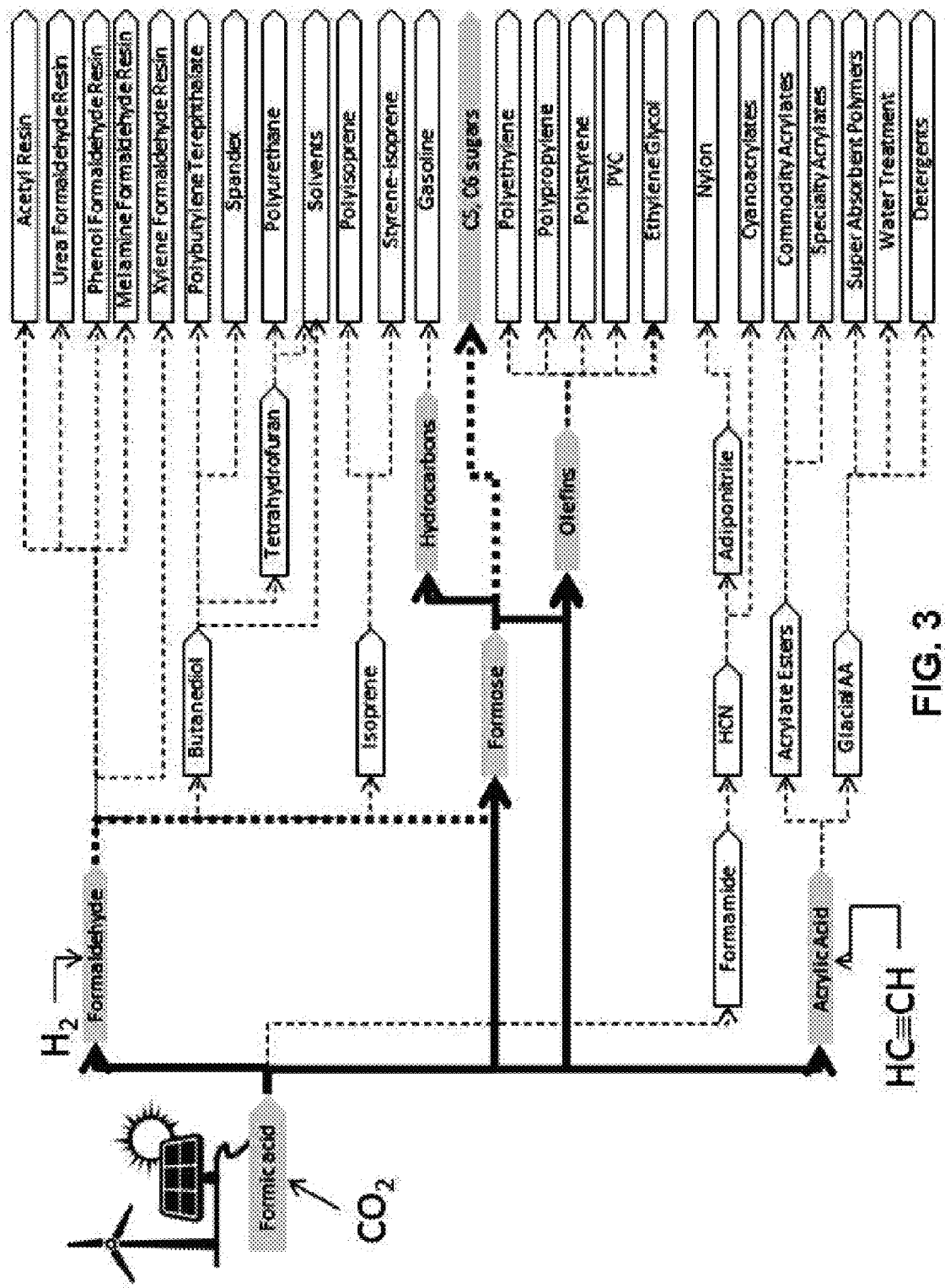
FIG. 3 is schematic diagram showing some of the products that can be synthesized from formic acid according to the teachings of the present application. The dashed lines are examples from conventional, prior art processes. The solid lines are examples of processes described in the present application.

The present process is not limited to the particular methodology, protocols, reagents described herein, as these can vary as persons familiar with the technology involved here will recognize. In addition, the terminology employed herein is for the purpose of describing particular embodiments only, and is not intended to limit the scope of the present process.

As used herein and in the appended claims, the singular forms "a", "an", and "the" include the plural reference unless the context dictates otherwise. Thus, for example, a reference to "a linker" is a reference to one or more linkers and equivalents thereof known to those familiar with the technology involved here. Also, the term "and/or" is used to indicate one or both stated cases may occur, for example A and/or B includes (A and B) and (A or B).

Unless defined otherwise, the technical and scientific terms used herein have the same meanings as commonly understood by persons familiar with the technology involved here. The features illustrated in the drawings are not necessarily drawn to scale, and features of one embodiment can be employed with other embodiments as persons familiar with the technology involved here would recognize, even if not explicitly stated herein.

Numerical value ranges recited herein include all values from the lower value to the upper value in increments of one unit, provided that there is a separation of at least two units between a lower value and a higher value. As an example, if it is stated that the concentration of a component or value of a process variable such as, for example, size, angle size, pressure, time and the like, is, for example, from 1 to 90, specifically from 20 to 80, more specifically from 30 to 70, it is intended that values such as 15 to 85, 22 to 68, 43 to 51, 30 to 32, and so on, are expressly enumerated in this specification. For values less than one, one unit is considered to be 0.0001, 0.001, 0.01 or 0.1, as appropriate. These are only examples of what is specifically intended and all possible combinations of numerical values between the lowest value and the highest value are to be treated in a similar manner.

Prior art references (patents and printed publications) referred to herein are incorporated by reference herein in their entirety.

Definitions

The term "Biological Reaction" refers to a chemical reaction that is taking place inside the cells of bacteria or yeast. "Biological reaction" also refers to reactions that use NADH or NADPH as a reactant.

The term "C5-C7 carbohydrates" refers to carbohydrates with 5 to 7 carbon atoms.

The term "Certified ACS" refers to a chemical that is certified to meet the specifications maintained by the American Chemical Society.

The term "EMIM" refers to the 1-ethyl-3-methylimidazolium cation.

The term "EMIM-BF4" refers to 1-ethyl-3-methylimidazolium tetrafluoroborate.

The term "FAH" refers to formate dehydrogenase.

The term "FDH" refers to formaldehyde dehydrogenase.

The term "Formose Reaction" refers to the polymerization of formaldehyde to carbohydrates. The reaction includes carbohydrates formed by direct condensation of formaldehyde, namely, $nH_2CO+H_2O \rightarrow HO(CH_2O)_nH$. The reaction also includes carbohydrates formed by adding formaldehyde to a solution with a dilute concentration of carbohydrates in order to create additional carbohydrates.

The term "Formose Sugars" refers to the carbohydrate products of the formose reaction.

The term "GC" refers to gas chromatography, a gas chromatograph instrument, or data from such an instrument represented as a gas chromatogram.

The term "ID" refers to inside diameter.

The term "NAD+" refers to nicotinamide adenine dinucleotide.

The term "NADH" refers to nicotinamide adenine dinucleotide, reduced.

The term "NADPH" refers to nicotinamide adenine dinucleotide phosphate, reduced.

The term "Non-Biological Reaction" refers to any chemical reaction other than a biological reaction.

The term "OD" refers to outside diameter.

The term "olefin" is an unsaturated chemical compound containing at least one carbon-to-carbon double bond; also referred to as an alkene.

The term "Organic Intermediate" refers to a molecule other than CO that contains at least one carbon atom. This term typically does not include salts containing the "inorganic" carbonate or bicarbonate anions, unless the compound also contains at least one additional carbon atom that is in an "organic" form, such as the carbon atoms in an acetate anion or a tetramethyl ammonium cation.

The term "SAPO" refers to a silico-alumino-phosphate zeolite.

The term "TPD" refers to temperature programmed desorption.

The term "UHV" refers to ultra-high vacuum.

Specific Description

Formic acid offers several advantages as a starting material for the production of fuels and chemicals. Co-owned U.S. patent application Ser. No. 12/830,338 (the '338 application) describes the synthesis of formic acid at high efficiency via a two-electron reduction of carbon dioxide. The process is efficient and is less expensive than other processes for the conversion of $CO_2$ into useful products.

The U.S. Food and Drug Administration lists formic acid as being generally recognized as safe for human consumption. A solution containing 85% formic acid in water is not spontaneously combustible, so it is safer to handle and transport than methanol.

Presently, however, formic acid is not used as a feedstock for industrial chemicals. See, for example, Wikipedia (http://en.wikipedia.org/wiki/Formamide; downloaded on Nov. 8, 2012), reporting that formamide can be formed via a reaction of formic acid and ammonia, but the process is no longer used industrially. Formic acid is also known to react with NADH or related compounds (for example, NADPH) in the presence of formaldehyde dehydrogenase to yield formaldehyde, but the process is impractical because NADH is very expensive. Formic acid can also react with lithium aluminum hydride and sodium borohydride to form formaldehyde at low selectivity but again the process is impractical on an industrial scale.

In particular, the present process includes a step in which formic acid is converted directly or indirectly via a non-biological reaction to at least one of formaldehyde, acrylic acid, ethylene, propylene, syngas, and C5-C7 carbohydrates, without a separate process step in which formic acid is first converted to methanol. Presently, none of these chemicals are synthesized from formic acid on an industrial scale. Formaldehyde is made industrially from the oxidation of methanol. Acrylic acid is made from the oxidation of propylene. Ethylene and propylene are usually made via cracking of petroleum, or from methanol via the methanol to olefins process. Syngas is usually made via steam reforming of natural gas, but it can also be made from petroleum or coal. Most methane comes from a natural gas well, although years ago it was also made from coal. C5-C7 carbohydrates are usually extracted from biomass.

In the present process, formic acid can be generated from conversion of carbon dioxide. Formic acid can also originate from other sources as long as the process includes a step in which formic acid is converted directly or indirectly to at least one of formaldehyde, acrylic acid, methane, ethylene, propylene, syngas, and C5-C7 carbohydrates, without a separate process step in which either (a) more than 10% of the formic acid is converted to methanol, or (b) NADH or an alkali or alkaline earth hydride reacts with the formic acid.

In the present process, carbon dioxide obtained from a natural source or from an artificial chemical source, which would otherwise be present in nature or which would be discharged by the artificial chemical source into the environment, is converted to formic acid. The formic acid is then converted to a mixture comprising at least one of formaldehyde, acrylic acid, ethylene, propylene, syngas, and C5-C6 carbohydrates.

In the present process for the production of formaldehyde, formic acid reacts over a metal oxide catalyst to yield a product comprising formaldehyde. Suitable metal oxides include CaO, SrO, BaO, $MnO_2$, $V_2O_5$, $Ta_2O_5$, $MoO_3$, $WO_3$, $TiO_2$, $TeO_2$, $Sb_2O_3$, $CeO_2$, $Sm_2O_3$, $Bi_2MoO_6$, $Ce_2(WO_4)_3$, $Bi_{12}TiO_{20}$, $PbTa_2O_6$, $Pb(VO_3)_2$ and $PbTiO_3$ and/or other oxides containing at least one of Ca, Sr, Ba, Mn, V, Ta, Mo, W, Ti, Te, Sn, Sb, Ge, Be, Sm, and Pb.

In the present process for the production of carbohydrates, formic acid is converted to formaldehyde, and the formaldehyde then reacts via either the formose reaction or an aldol condensation to yield carbohydrates.

In the present process for the production of organic acids, formic acid reacts with an alkene or alkyne to yield an organic acid with at least 3 carbon atoms. The present process forms acrylic acid by reacting formic acid with acetylene in the presence of a catalyst comprising at least one of Cu, Ni, Fe, Co, Mn, Cr, Ag, Pd, Ru, Rh, Mo Au, Pt, Ir, Os, Re, and W. The present process employs homogeneous catalysts comprising one or more of Cu, Ni, Fe, Co, Mn, Cr, Ag, Pd, Ru, Rh, Mo Au, Pt, Ir, Os, Re, and W, in which the catalyst is active for the reaction between formic acid and acetylene.

Without further elaboration, it is believed that persons familiar with the technology involved here, using the preceding description, can employ the present process to the fullest extent. The following examples are illustrative only, and not meant to be an exhaustive list of all possible embodiments, applications or modifications of the present process.

Example 1

Conversion of Carbon Dioxide to Formic Acid

Example 1 illustrates the conversion of carbon dioxide to formic acid, using a modification of the methods in applicant's co-owned U.S. patent application Ser. No. 12/830,338. By way of background, electrolysis of $CO_2$ to formic acid had been well known in the literature, but prior to the '338 application those processes exhibited poor energy efficiency. The process described in the '338 application was the first to demonstrate high energy efficiency, but the rate was insufficient.

The present example provides a method to produce formic acid at a high efficiency and an improved rate. To provide the environmental benefit of effecting a net reduction in the amount of carbon dioxide greenhouse gas in the atmosphere, it is preferred that the $CO_2$ starting material be obtained from sources in which the $CO_2$ would otherwise have been released into the atmosphere, such as combustion, fermentation, or the manufacture of cement or steel. The $CO_2$ could also be obtained from existing sources, such as in natural gas or oil deposits (including fields in which $CO_2$ injection has been used for enhanced oil recovery), in subterranean pockets or pore spaces rich in $CO_2$, or even in the atmosphere itself. It is also preferred that the energy required for the conversion of $CO_2$ to formic acid would originate from a carbon-neutral energy source, such as wind, solar, hydroelectric, tidal, wave, geothermal and/or nuclear.

Figure 4:
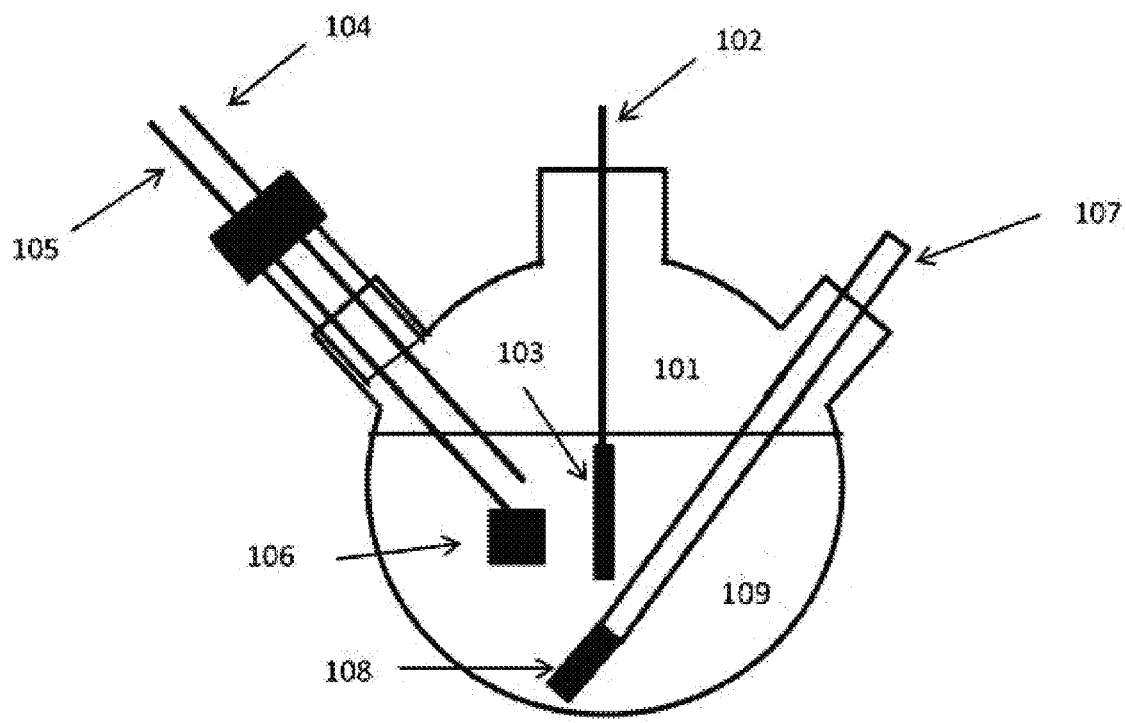
FIG. 4 is a schematic of the electrochemical cell employed in Example 1 herein.

As illustrated in FIG. 4, the electrochemical cell employed in Example 1 includes a three-necked flask 101, palladium wire 102, working electrode 103 (comprising carbon paper with palladium catalyst), reference electrode 104 (silver wire), platinum wire 105, counter electrode 106 (platinum mesh), glass tube 107 for sparging gas, glass frit 108, and electrolyte 109.

More specifically, the experiments in Example 1 employed a 15 mL three necked flask 101. Glass sparging tube 107 with glass frit 108 was used to inject the gas. Silver wire 104 was used as reference electrode. The counter electrode 106 was made by attaching a 25×25 mm platinum mesh 105 (size 52) (Alfa-Aesar, Ward Hill, Mass.) to a 5 inch platinum wire (99.9%, 0.004 inch diameter). The working electrode was formed using a palladium wire 102 attached to carbon fiber paper 103 (GDL 35 BC, Ion Power, Inc., New Castle, Del.) with palladium black (Alfa-Aesar, Ward Hill, Mass.) painted on both sides.

Prior to carrying out the experiments, the glass parts and the counter electrode were put in a 50/50 v/v sulfuric acid/water bath for at least 12 hours, followed by rinsing with Millipore filtered water (Millipore Corporation, Billerica, Mass., USA). Later, they were placed in an oven at 120° C. to remove residual water.

During the experiment, a catalyst ink comprising a catalytically active element (palladium) was prepared as follows: First 0.01 grams of palladium black (99.9% metals basis, Alfa-Aesar, Ward Hill, Mass.) was mixed with 600 μL of Millipore water, 600 μL of Millipore isopropanol and 2 drops of Nafion solution (5%, 1100EW, DuPont, Wilmington, Del.) The mixture was sonicated for 3 minutes. In the meantime, carbon paper with dimensions of 1 cm×2.5 cm was cut and placed under a heat lamp. Later, palladium ink was painted on carbon paper with a painting brush under the heat lamp. After drying under a heat lamp for 30 min, the procedure was repeated again to paint the palladium catalyst on the other side of the carbon paper. The painting process was repeated until substantially all of the ink was transferred onto the carbon paper. The carbon paper was then dried in the air overnight. This yielded a catalyst with physical surface area of 4 mg/cm$^2$.

Electrolyte 109 was prepared by mixing 5 mL of Millipore water and 5 mL of EMIM-BF4 (≥97%, Sigma Aldrich, St. Louis, Mo.) to obtain 50% volume ratio ionic liquid solution. The mixture was then poured into the three neck flask 101. Next, ultra-high-purity (UHP) argon was fed through the sparging tube 107 and glass frit 108 for 30 minutes. Before carbon dioxide conversion, the carbon dioxide was bubbling through the sparging tube 107 for at least 30 min Next, the working electrode, counter electrode and reference electrode were all connected to an SI 1287 Solartron electrical interface (Solartron Analytical, Schaumburg, Ill., USA). Then, a chronoamperametric measurement was performed by stepping from open cell potential to −1.5V vs. Ag/AgCl.

The reaction was run for two days, and 750 µL samples were periodically taken out of the mixture for analysis by GC.

The GC analysis procedure was carried out as follows. The 750 µL sample was placed in a GC injection vial. 110 µL methanol and 75 µL 0.1M sulfuric acid were injected into the vial to functionalize the formic acid to methyl formate. After 90 minutes, the head space over the sample was injected into an Agilent 6980N GC and the methyl formate peak area was calculated. A calibration curve was used to compute how much formic acid was formed.

Figure 5:
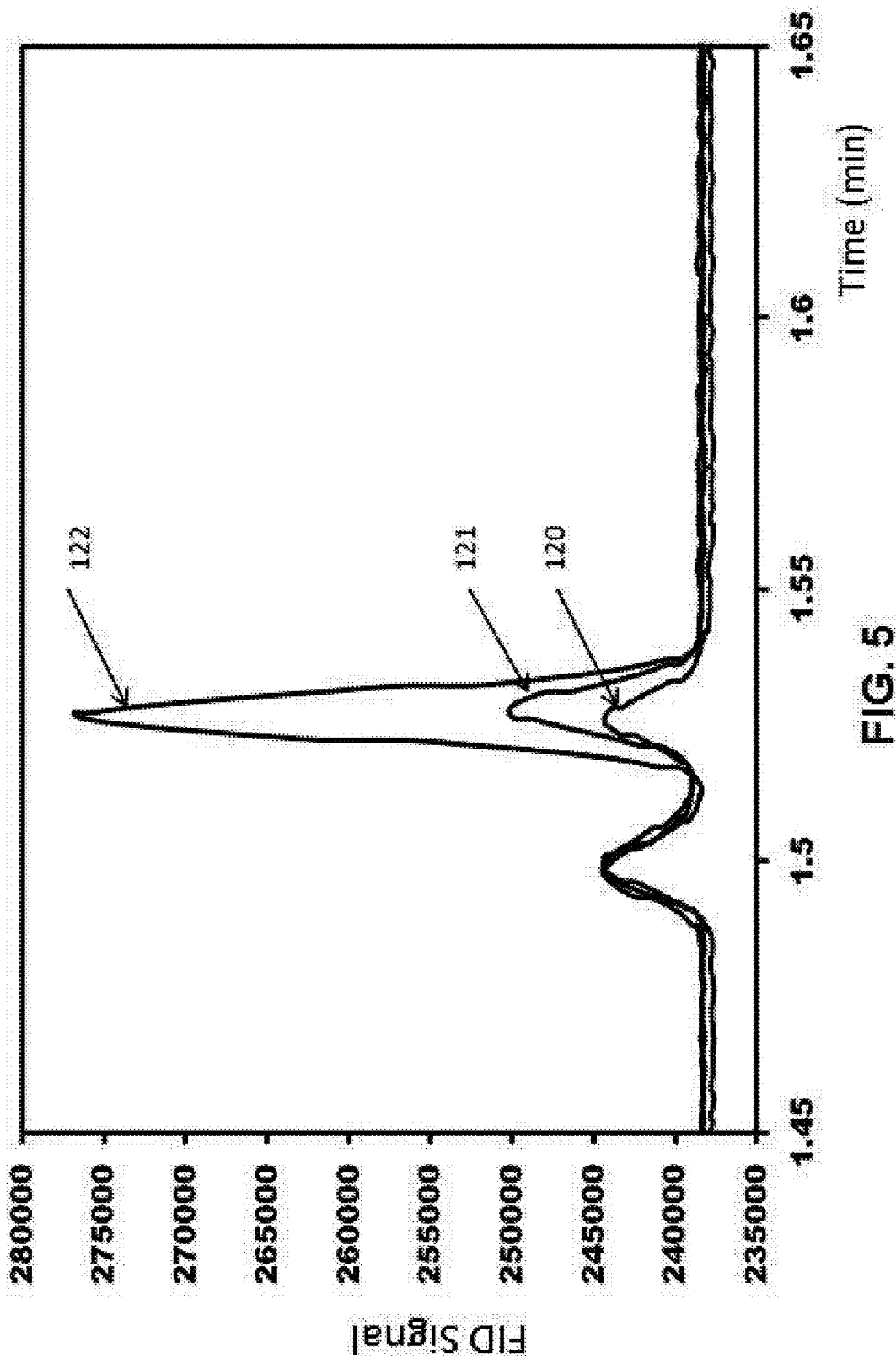
FIG. 5 is a gas chromatogram (GC) trace taken during $CO_2$ conversion to formic acid following the procedures in Example 1 herein.

FIG. 5 shows how the GC trace of the functionalized formic acid grew with time. Clearly, formic acid was being produced in the reactor. The gas chromatogram (GC) trace shown in FIG. 5 was a taken during $CO_2$ conversion to formic acid following the procedures in Example 1 herein. The samples were taken after 1370 minutes (peak 120), 1850 minutes (peak 121), and 2900 minutes (peak 122). The peak near 1.53 minutes is associated with formic acid. The peak near 1.50 minutes is associated with the methanol used to functionalize the formic acid.

Example 2

Hydrogenation of Formic Acid to Formaldehyde

The objective of Example 2 is to demonstrate that formic acid can be hydrogenated to formaldehyde using catalysts such as $CeO_2$ and $TeO_2$. By way of background, formaldehyde is currently made industrially via oxidative dehydrogenation of methanol. In 1912, Sabatier and Maihe (Compt. Rend., 152: pages 1212-1215 (1912); "the Sabatier paper") reported that formic acid reacts on one of two pathways on most metals and metal oxides, namely: a dehydrogenation pathway:

$$HCOOH \rightarrow H_2 + CO_2 \qquad (1)$$

or a dehydration pathway:

$$HCOOH \rightarrow H_2 + CO \qquad (2)$$

Sabatier's paper further indicates that formaldehyde ($H_2CO$) can form at low rates during formic acid decomposition on a thorium oxide ($ThO_2$) catalyst, via the reaction:

$$2HCOOH \rightarrow H_2O + H_2CO + CO_2 \qquad (3)$$

The rates of these reactions are too small to be practical, however. Barteau and coworkers also found transient formaldehyde formation via reaction 3 during TPD of formates in UHV (H. Idriss, V. S. Lusvardi, and M. A. Barteau, Surface Science 348(1-2), pages 39-48 (1996); K. S. Kim and M. A. Barteau, Langmuir 6(9): pages 1485-1488 (1990). Górski et al. (Journal of Thermal Analysis, Vol. 32, pages 1345-1354 (1987)) found traces of transient formaldehyde formation in a reaction between metal formates and $NaBH_4$. Formate ions can also react with NADH or NADPH on formaldehyde dehydrogenase (FDH) to form formaldehyde. Still, except for processes using NADH or NADPH, there is no apparent evidence from the published journal or patent literature that formic acid could be converted to formaldehyde at steady state with selectivities above 5 percent, where the selectivity is calculated as Selectivity=(moles of formaldehyde formed)/(moles of formic acid used).

This is insufficient for industrial practice. Processes involving NADH or NADPH or microbes are also too expensive to be used in most industrial production.

The present process provides a route to the conversion of formic acid to formaldehyde at high selectivity via the reaction

$$HCOOH + H_2 \rightarrow H_2O + H_2CO \qquad (4)$$

The reviews of formic acid decomposition by Trillo et al. (Catalysis Reviews 7(1), pages 51-86, (1972)) and by Mars (Advances in Catalysis 14, pages 35-113 (1963)) contain no mention of reaction (4) above. Similarly, the review of ceria catalysis by Trovarelli (Catalysis Reviews: Science and Engineering 38:4, pages 439-520 (1996)) and by Ivanova (Kinetics and Catalysis, Vol. 50, No. 6, pages 797-815 (2009)) contain no mention of reaction (4) above.

Figure 6:
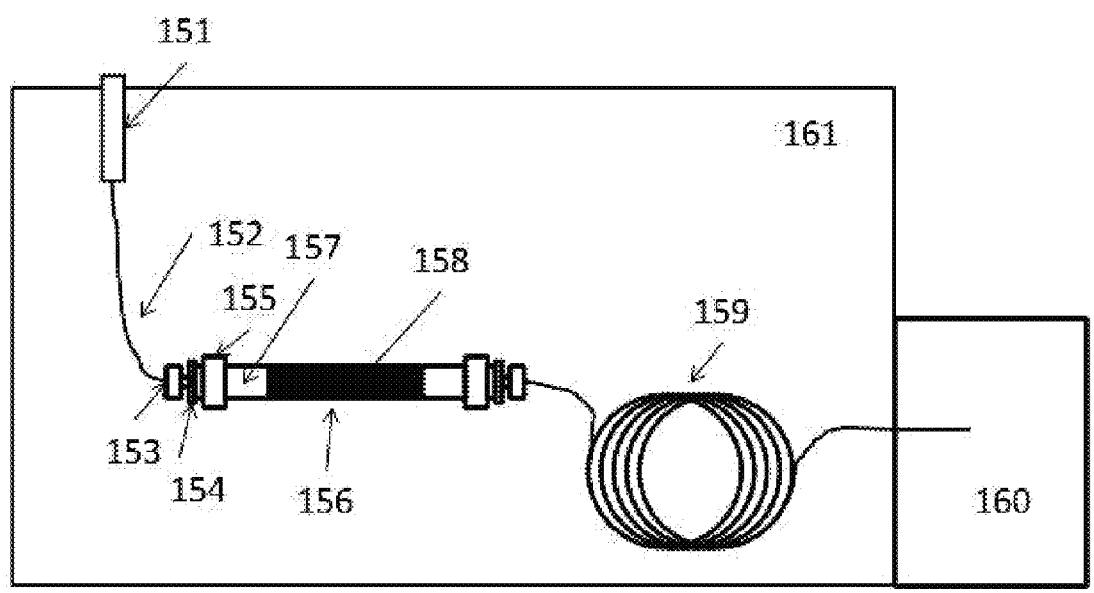
FIG. 6 is a schematic diagram of the experimental apparatus for the conversion of formic acid to formaldehyde in Example 2 herein.

The experimental apparatus for the conversion of formic acid to formaldehyde in Example 2 is shown in FIG. 6. The experimental apparatus includes GC injector coupled with an Agilent 7683B autosampler 151, intermediate polarity (IP) deactivated capillary guard column 152 (length=30 cm, inside diameter=250 µm), 1/16 inch nut 153, reducing 1/16 inch to 1/8 inch reducing union 154, 1/8 inch nut 155, glass tube 156 (7.6 cm length, 3 mm OD, 1.75 mm ID), quartz wool 157, catalyst 158, Zebron ZB-WAX-Plus capillary GC column 159 (30 m×250 µm×0.25 µm), Agilent 5973N Mass Selective Detector (MSD) 160, and Agilent 6890N GC oven 161.

In the experiments of Example 2, catalyst 158 were packed into glass tube 156, and quartz wool plugs 157 were inserted into both ends of the glass tube to hold the catalyst. The entrance of the catalyst packed glass tube 156 was connected to IP deactivated guard column 152 with 1/16 inch nut 153, reducing union 154, and 1/8 inch nut 155. IP deactivated guard column was connected to a GC injector that coupled with an Agilent 7683 autosampler 151, while the exit of the catalyst packed glass tube 156 was connected to a Zebron (Phenomenex, Torrance, Calif.) ZB-WAX-Plus capillary GC separation column 159 (30 m×250 µm×0.25 µm). The other side of the GC separation column 159 was inserted into 5973 N MSD 160. The entire apparatus was placed into an Agilent 6890 N GC oven 161.

Prior to the experiments, the catalysts, such as cerium (IV) oxide (99.9% metal basis from Alfa Aesar, Ward Hill, Mass.) and tellurium (IV) oxide (99.9% metal basis from Alfa Aesar, Ward Hill, Mass.) were conditioned in a box oven (Lindberg/Blue M from Thermo Electron Corporation) at 250° C. for 4 hours. Cerium oxide pieces (3-6 mm) were granulated to 20-100 mesh particles before packing.

The borosilicate glass tube (trade designation Pyrex, Corning Inc., Corning, N.Y.) was cleaned with acetone (certified ACS from Fisher Scientific), and then rinsed with Millipore filtered water (Millipore Corporation, Billerica, Mass., USA) and dried at 100° C. before catalyst packing. The catalyst packed bed was prepared by pouring the catalysts (0.2 to 0.5 gram) into a glass tube with shaking or tapping. The tube was first positioned vertically against the workbench, the lower end of the tube was filled with quartz wool (serving as a frit to hold catalyst particles) and the upper end was attached to a funnel into which the solid catalysts were fed. The shaking or tapping reduced voids in the tube and facilitated tight packing. Before the performance test the packed bed column was purged with hydrogen (1.5 ml/min) at 100° C. for 2 to 4 hours.

Experiments were performed on an Agilent Model 6890N gas chromatograph equipped with a Model 5973N quadrupole mass selective detector (MSD) and Model 7683 autosampling unit. 0.2 µL of formic acid (Fluka, ~98% from Sigma Aldrich, St. Louis, Mo.) was injected into the GC with the 7683 autosampler; the injector was maintained at 200° C. with a split ratio of 100:1. The vaporized formic acid was introduced to the catalyst bed with hydrogen, and the products from the catalyst bed were separated using a Zebron (Phenomenex, Torrance, Calif.) ZB-WAX-Plus column (100% polyethylene glycol), 30 m long with a 250 µm I.D. and 0.25 µm film thickness. The carrier gas was hydrogen, which was set at a constant flow rate of 1.1 mL/min with a head pressure of 2.9 psi at 100° C. The transfer line was set at 200° C. The column oven temperature was set at 100° C. or 150° C. isothermal for the testing of the $CeO_2$ packed bed. Mass selective detector detection was performed at 230° C. with either full scan (15-150 amu) for identification or with selected ion monitoring (SIM) mode for quantitative analysis. The qualifying ions for SIM mode were m/z 30 for formaldehyde (m/z 30 from formic acid is very weak). Chromatographic data were collected and evaluated using MSD Productivity Chemstation Software.

Figure 7:
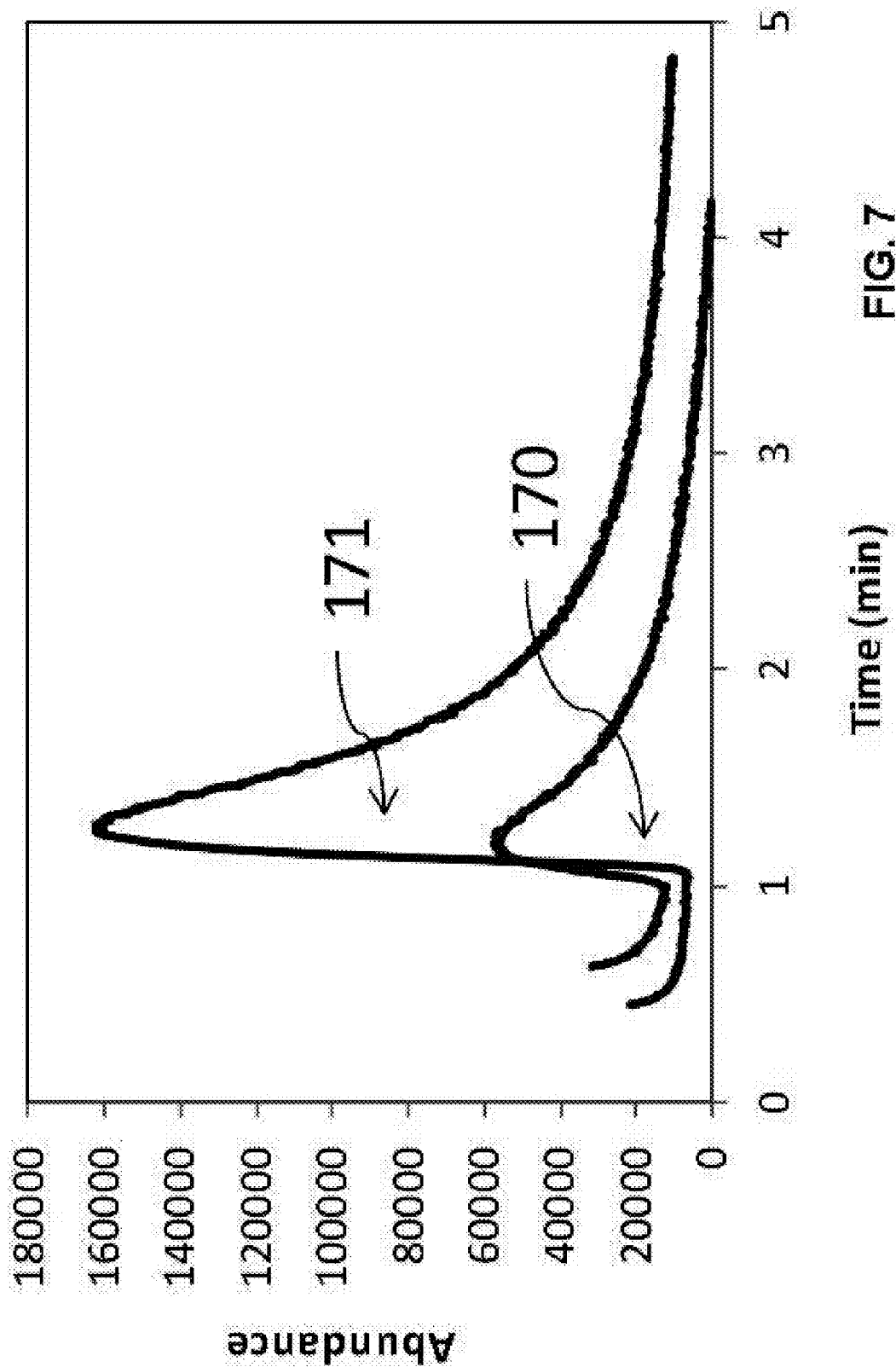
FIG. 7 is a mass spectrogram showing the m/z=30 ion (formaldehyde) observed during formic acid hydrogenation on a $CeO_2$ catalyst at 100° C. (plot 171) and 150° C. (plot 170).

FIG. 7 shows the abundance of the formaldehyde GC trace at different temperatures from the $CeO_2$ catalyst bed. Significant formaldehyde formation started to be observed at bed temperatures of 40° C. The rate of formaldehyde formation increased as the temperature was raised to 60° and 80° C., then there was a slow decay at higher temperatures. The optimal temperature was between 60° C. and 100° C. Very little formaldehyde was detected at temperatures above 20° C. These results demonstrate that formic acid can be hydrogenated to formaldehyde with high selectivity without first converting the formic acid to methanol. Further, the process performs well at temperatures much lower than the 500-600° C. used to produce methanol commercially.

Similar tests were performed with $TeO_2$ and significant formaldehyde production was also found, as summarized in Table 1 below.

TABLE 1

Conversion and selectivity of the catalysts for formic acid hydrogenation to formaldehyde

| Catalyst | Optimized Temperature | Conversion | Approximate Selectivity |
|---|---|---|---|
| $CeO_2$ | 80° C. | 64% | ~80% |
| $TeO_2$ | 80° C. | 34% | ~85% |

One can speculate how this reaction occurs. Previous workers have found that an adsorbed formyl intermediate (H—C=O) forms during formic acid dehydration (namely, reaction (2) above) on most metal oxides. It is proposed here that the formyl species is being hydrogenated to yield formaldehyde. The formyl intermediate can form on the oxides of Mg, Ca, Sr, Ba, Ti, Y, Lu, Ti, Zr, Hf, V, Nb, Ta, Cr, Mo, W, Fe, Co, Ni, Cu, Zn, Al, Ga, In, Tl, Si, Ge, Sn, Sb, Bi, Se, Te, Pb, La, Ce, Pr, Th, Nd, Pm, U, Sm, Eu, Gd, Tb, Dy, Ho, Er, Tm, and Yb. Therefore it is believed that catalysts comprising the oxides of Mg, Ca, Sr, Ba, Ti, Y, Lu, Ti, Zr, Hf, V, Nb, Ta, Cr, Mo, W, Fe, Co, Ni, Cu, Zn, Al, Ga, In, Tl, Si, Ge, Sn, Sb, Bi, Se, Te, Pb, La, Ce, Pr, Th, Nd, Pm, U, Sm, Eu, Gd, Tb, Dy, Ho, Er, Tm, and/or Yb are active for formic acid hydrogenation to formaldehyde. Generally the formyl species is stable up to about 350° C. Therefore, it is expected that the reaction temperature should be below 350° C. This compares to 500-600° C. in the conventional synthesis of formaldehyde. It is also believed that the temperature should be above 8° C., as formic acid freezes at 8.4° C.

Example 3

Conversion of Formic Acid to C5-C6 Carbohydrates

The objective of Example 3 is to demonstrate that carbohydrates can be formed from formic acid. By way of background, the conversion of formaldehyde to mixed carbohydrates via the formose reaction is known. For example, the reaction $$nH_2CO + H_2O \rightarrow HO(CH_2O)_nH \quad (5)$$

is disclosed in U.S. Pat. Nos. 2,224,910, 2,760,983, and 5,703,049, and in Iqbal and Novalin, Current Organic Chemistry 16, page 769 (2012; "the Iqbal paper"). See also Shigemasa et al., Bul. Chem. Soc. Japan 48, page 2099 (1975). It is believed that there is no previous report of carbohydrate synthesis starting with formic acid. The present process provides such a procedure, namely:

(1) Converting the formic acid to formaldehyde according to the procedures set forth in Example 2 herein;
(2) Reacting the formaldehyde via the methods described in U.S. Pat. Nos. 2,224,910 and 2,760,983 to form a mixture of C3 to C7 carbohydrates.

In the remainder of this section, an improved procedure for step (2) above will be provided, which produces mainly C5 and C6 sugars.

In Example 3, 40 mL of deionized water was mixed with 4.5 mL of 37% formaldehyde. This solution was heated to 60° C. for an hour. After temperature stabilization, 425 mg of $Ca(OH)_2$ was added to the solution. The reaction was run under $N_2$ gas flow (200 sccm), with magnetic stirring for homogeneity. 1 mL aliquots were taken at 30 minutes and 45 minutes, and then the heat was turned off (but the $N_2$ flow and stirring remained active for another 1.5 days). One final aliquot was taken after 1.5 days. Table 2 below shows the products formed after 1.5 days. The liquid chromatography (LC) analysis here identified three major species, C6 sugars, C5 sugars, and calcium salts of C6 sugars. Tandem mass spectrometry (MS/MS) of the C6 fragments showed that the C6 sugars consisted of either glucose or galactose, or a mixture of the two.

TABLE 2

| Products formed in Example 3 | |
|---|---|
| C5 sugars | 5% |
| C6 sugars | 85% |
| Calcium salt of C6 | 10% |

These results demonstrate that formic acid can be converted to a mixture of C5 and C6 sugars without first converting the formic acid to methanol.

Example 4

Conversion of Formic Acid to Olefins (Ethylene, Propylene, Butene)

The objective of Example 4 was to demonstrate the conversion of formic acid to olefins such as ethylene, propylene and butene. Example 4 illustrates the manufacturing of olefin gas from formose sugar in the presence of the zeolite catalyst SAPO-34. By way of background, U.S. Pat. Nos. 4,503,278, 4,549,031, 6,437,208, 6,441,262, 6,964,758, 7,678,950, 7,880,049, 8,148,553, and 8,231,857 disclose that carbohydrates can be converted to hydrocarbons by a number of different processes. In each case, the processes start with pure sugar solutions with no basic impurities such as calcium. A further objective of Example 4 is to demonstrate that olefins can be produced without removing the calcium.

The experiments of Example 4 were carried out under static conditions. 179 mL of formose sugar solution/calcium solution was synthesized as described in Example 3 without further purification. $CO_2$ was bubbled through the mixture to lower the pH to 6.2, and the precipitate was removed by filtration. The formose sugar solution and 18 grams of SAPO-34 (Sigma-Aldrich, Milwaukee, Wis.) were charged into an Alloy C276 pressure reaction apparatus with a capacity of 600 mL (Parr Instrument Company, Moline, Ill.) designed for a maximum working pressure of 3000 psi at 350° C. The reactor had facilities for gas inlet, gas and liquid outlet, cooling water inlet and outlet, temperature controlled external heating and variable agitation speed. A Parr 4843 controller (Parr Instrument Company, Moline, Ill.) was used to control the heating and stirring speed and to monitor the reactor's real temperature and pressure. After purging the reactor with nitrogen gas (S.J. Smith Co., Urbana, Ill.) for about 4 minutes, the gas inlet and outlet were then closed. The reactor was then heated to 300° C. within 40-50 minutes, whereby system pressure increased to 1300 psi. The reaction proceeded at 300° C. for 12-15 hours, and then the reaction system was cooled to room temperature.

Figure 8:
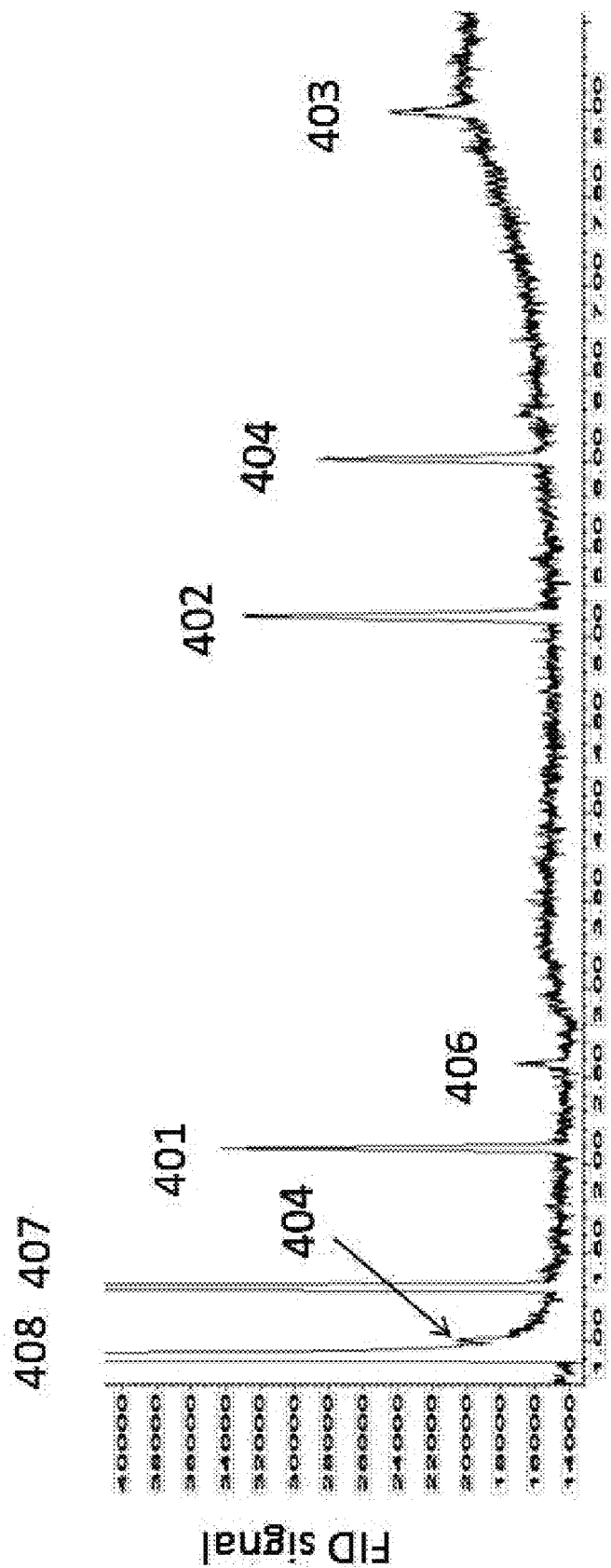
FIG. 8 is a GC trace demonstrating the formation of ethylene (peak 401), propylene (peak 402) and butene (peak 403) in Example 4 herein. Other products include dimethylether (peak 404), methane (peak 405), ethane (peak 406) and $CO_2$ (peak 407), as well as air (peak 408).

A gas phase sample was collected with a Tedlar bag and analyzed with an Agilent Model 6890N gas chromatograph equipped with a Model 5973N quadrupole mass selective detector (MSD) and Model 7683 autosampling unit. A 5 µL gas sample was injected into the GC with 7683 autosampler, and the injector was maintained at 250° C. with a split ratio of 10:1. Compounds were separated using a GS-Carbon PLOT column (Agilent Technologies, Santa Clara, Calif.), 27 m length with a 320 µm I.D. and 3.0 µm film thickness. The carrier gas was helium and was set at a constant flow rate of 2.5 mL/min with a head pressure of 5.91 psi at 40° C. The transfer line was set at 200° C. The column oven temperature was programmed from 40° C. to 200° C. with ramping rate at 20° C./min. Mass selective detector detection was performed at 230° C. with full scan (15-300 amu) for identification. As shown in FIG. 8, olefin gases such as ethylene, propene and butene were detected in the gas phase, and small amounts of methane and ethane were also detected.

Example 5

Conversion of Formic Acid to Propylene

The objective of Example 5 is to demonstrate that formic acid can be converted to propene. By way of background, U.S. Pat. Nos. 4,503,278, 4,549,031, 6,437,208, 6,441,262, 6,964,758, 7,678,950, 7,880,049, 8,148,553, and 8,231,857 disclose that carbohydrates can be converted to fuels or olefins by a number of different processes but generally a mixture of a large number of hydrocarbons is produced. Here, a process is described that produces mainly propylene with smaller amounts of butene and ethylene. An important aspect of the processes is to not use naturally occurring carbohydrates as a starting material. Instead, carbohydrates produced by the Formose Reaction can be used as a starting material, and the carbohydrates then converted to hydrocarbons.

The procedure used in Example 8 was identical to that in Example 5 except that ZSM-5 (Sigma-Aldrich, Milwaukee, Wis.) was substituted for the SAPO-34, and the reaction was run for only 4 hours.

Figure 9:
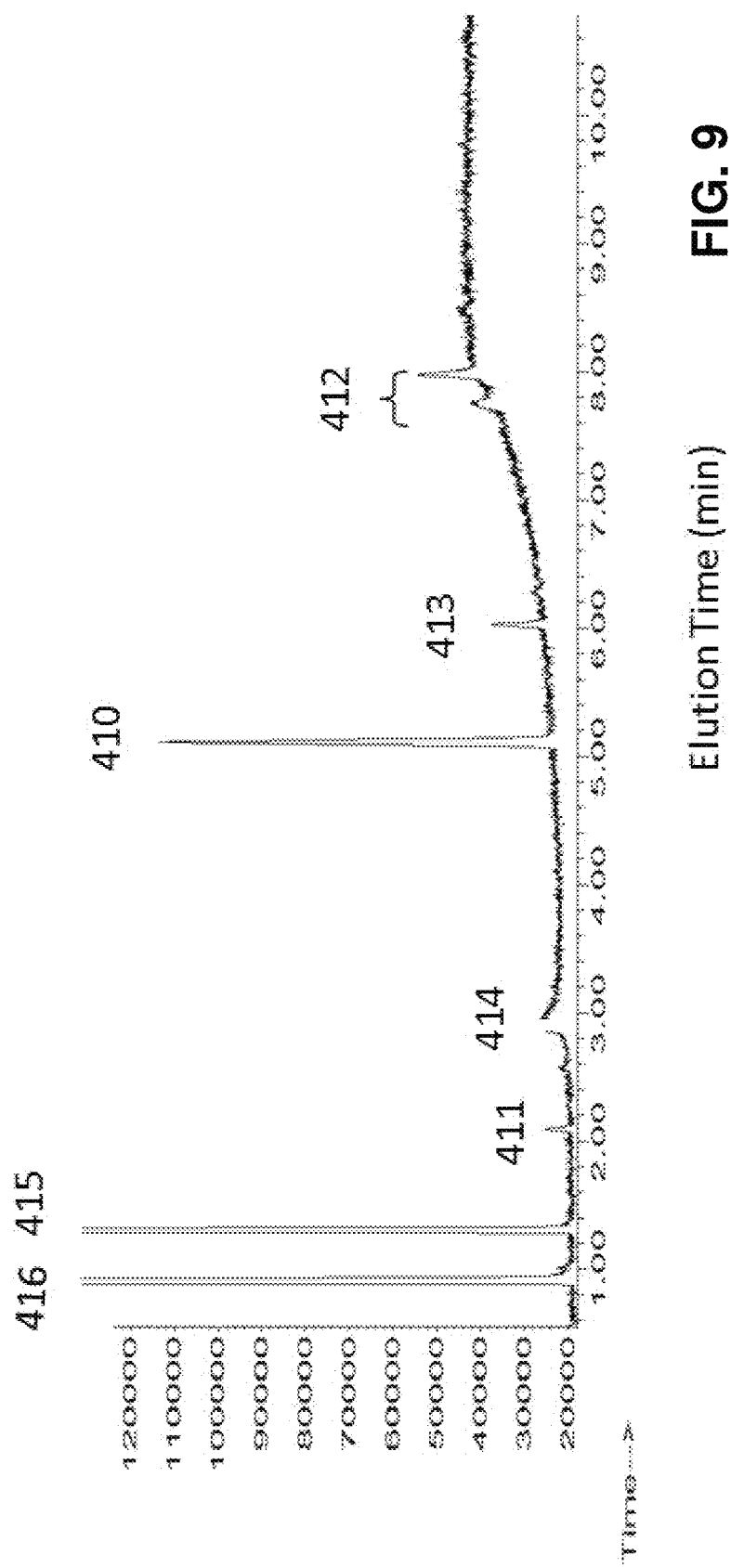
FIG. 9 is a GC trace demonstrating the formation of propylene (peak 410) in Example 5 herein. Other products include ethylene (peak 411), butene (peak 412), dimethylether (peak 413). Also seen in the trace are water (peak 414), $CO_2$ (peak 415) and air (peak 416).

FIG. 9 shows a GC trace taken from the gas phase at the end of the process. The magnitude of propylene peak 410 indicated that propylene was the major reaction product, with the lesser magnitudes of ethylene peak 411 and butene peak 412 indicating that ethylene and butene were present in much smaller quantities. Dimethyl ether peak 413, water peak 414. $CO_2$ peak 415, and air peak 416 indicate the presence of those constituents, but they are not reaction products.

Example 8 shows that ZSM-5 can be used to convert formic acid to propylene with reasonably high selectivity.

It is also known that propylene can be converted to hydrocarbon fuels using a process called alkylation. In the present process for the formation of hydrocarbon fuels, formose sugars are converted to hydrocarbon fuels. In particular, the present process employs zeolite catalysts such as ZSM-5 in the conversion of formic acid and/or formose sugars to hydrocarbon fuels.

U.S. Pat. Nos. 4,503,278, 4,549,031, 6,437,208, 6,441,262, 6,964,758, 7,678,950, 7,880,049, 8,148,553, and 8,231,857 disclose many other catalysts that can be used to convert oxygenates to hydrocarbons. The present process encompasses the use of catalysts disclosed in these prior patents in the conversion of formic acid to hydrocarbons.

Example 6

Conversion of Formic Acid to Acrylic Acid

The objective of Example 6 is to demonstrate that formic acid can be converted to acrylic acid ($H_2C=CHCOOH$). By way of background, acrylic acid is currently made by oxidation of propylene. U.S. Pat. Nos. 2,806,040, 2,925,436 and 2,987,884 disclose that acrylic acid can also be made via the reaction:

$$CO + H_2O + HC \equiv CH \rightarrow H_2C = CHCOOH \qquad (6)$$

This reaction is not commercially practical, however, because high pressures and temperatures are required.

Reaction (5) above provides a route to the conversion of formic acid to acrylic acid. The process is as follows:
 (1) Formic acid is reacted on a strongly acidic cation exchange resin, such as one available under the trade designation Dowex 50WX8 hydrogen form (Sigma Aldrich, St. Louis, Mo.) to yield CO and $H_2O$ via reaction (2) as was demonstrated in Example 2 above.
 (2) The CO is purified by removing water.
 (3) The CO and water are reacted with acetylene at 100 atm and 200° C. on a nickel bromide catalyst according to the teachings of U.S. Pat. Nos. 2,806,040, 2,925,436 and U.S. Pat. No. 2,987,884 to yield acrylic acid.

This is not the only way to create acrylic acid from formic acid without going through methanol as an intermediate. In particular, Example 6 illustrates the manufacturing of acrylic acid or its derivatives from formic acid and acetylene via the reaction:

$$HCOOH + HC\equiv CH \rightarrow H_2C=CHCOOH \quad (7)$$

in the presence of palladium acetate and phosphine ligand under mild conditions. Tang, et al. (Journal of Molecular Catalysis A: Chemical 314, pages 15-20 (2009)) had previously demonstrated that trifluoromethane sulfonic acid-promoted palladium acetate can catalyze reaction (6) above under mild conditions. The example below demonstrates that reaction (7) above can also occur under similar conditions.

Figure 10:
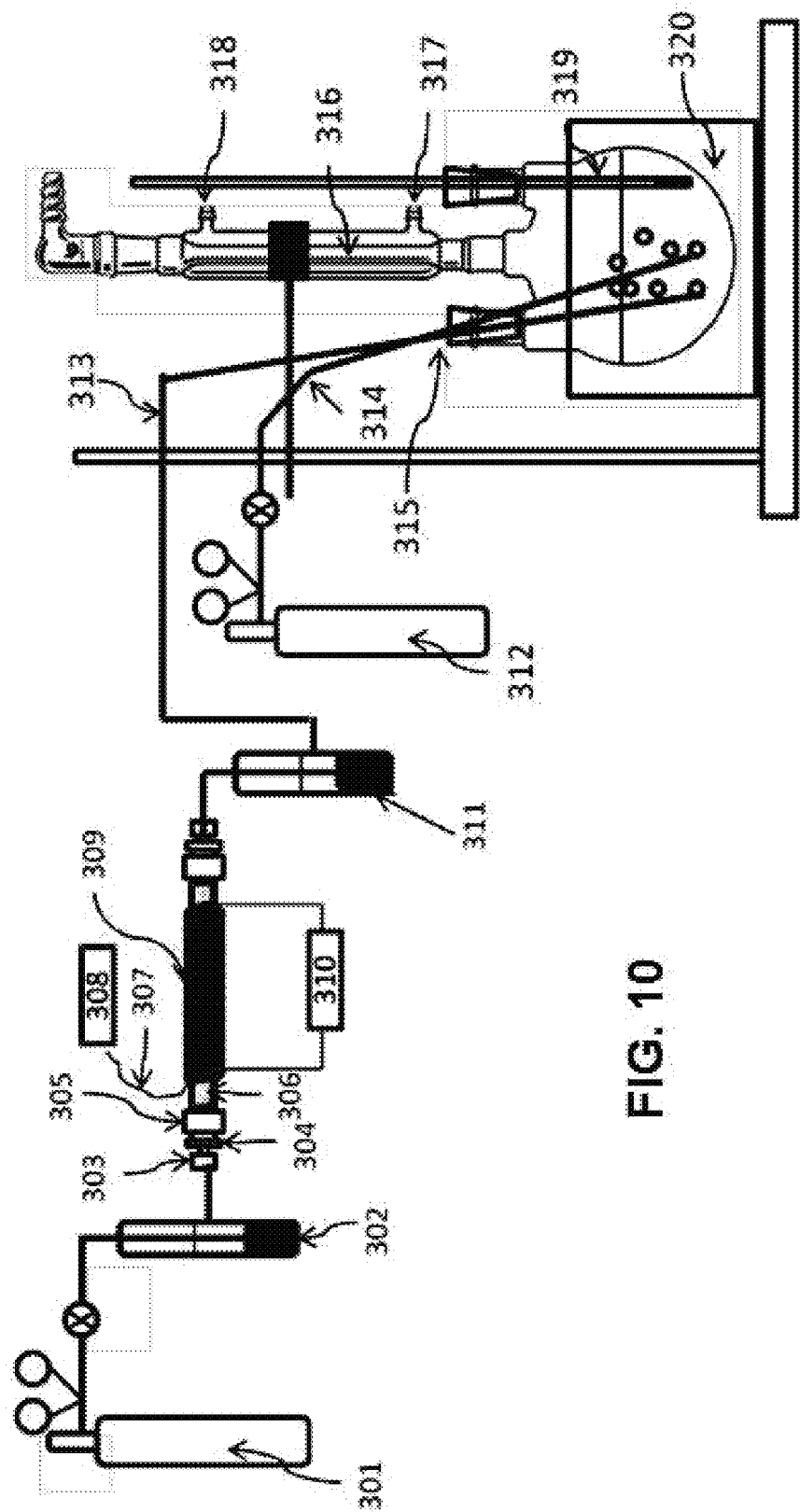
FIG. 10 is a schematic diagram of the apparatus employed to convert formic acid and acetylene to acrylic acid in Example 6 herein.

The experimental apparatus for Example 6 is shown in FIG. 10. Catalyst packed bed 306 was constructed from a glass tube packed with ion exchange resin, available under the trade designation Dowex 50WX8, with quartz wool plugs at both ends. A K-type thermocouple 307 was held snugly against the outer glass wall and a flexible electric heating tape 309 (Cole Parmer, Vernon Hills, Ill.) was coiled around the glass tube to create a heated region. The temperature of catalyst packed bed 306 was measured with thermocouple thermometer 308 (Barnant 100, Barnant Company, Barrington, Ill., USA). A Variac W10MT3 autotransformer 310 (Variac, Cambridge, Mass.) was used to apply adjustable voltage to the heating tape 309. The upstream end of catalyst packed bed 306 was connected to a bubbler 302 that contained formic acid with a ¹⁄₁₆ inch nut 303, a ¹⁄₁₆ inch to ⅛ inch reducing union 304, a ⅛ inch nut 305, and ⅛ inch Tygon tubing. The downstream end of catalyst packed bed 306 was attached to a bubbler 311, which contained concentrated $H_2SO_4$. The resultant gas was introduced into the reaction mixture by a stainless steel needle 313. A water condenser 316, thermometer 319, CO gas line 313 and acetylene gas line 314 were connected to a 3-neck flask immersed in a 55° C. water bath 320.

Prior to carrying out the reaction, the Dowex 50WX8 catalyst was air dried overnight and the Pyrex glass tube was cleaned with acetone (certified ACS from Fischer Scientific), then rinsed with Millipore filtered water (Millipore Corporation, Billerica, Mass., USA), and dried at 100° C. before catalyst packing. The catalyst packed bed was prepared by pouring 1.3435 grams of catalyst into a glass tube with shaking or tapping. The tube was first positioned vertically against the workbench, the lower end of the tube was filled with quartz wool (serving as a frit to hold catalyst particles), and the upper end was attached to a funnel into which the solid catalysts were fed. The shaking or tapping reduced voids in the tube and facilitated tight packing.

The experiments were carried out under dynamic conditions. A mixture of 50 mL of acetone (Fisher Scientific), 10 mL of deionized (DI) water, 0.01150 grams of palladium acetate (Sigma-Aldrich, Milwaukee, Wis.), 0.3989 grams of diphenyl-2-pyridylphosphine (Sigma-Aldrich, Milwaukee, Wis.), 0.3742 g inhibitor hydroquinone (Sigma-Aldrich, Milwaukee, Wis.) and 0.29 ml trifluoromethane sulfonic acid (Sigma-Aldrich, Milwaukee, Wis.) were charged into a 100 mL 3-neck flask (Chemglass, Vineland, N.J.) The reaction temperature was controlled with a water bath and set at 50-55° C. Formic acid (Fluka, ~98% from Sigma Aldrich) vapor from the first bubbler 302 was introduced into the catalyst packed bed by nitrogen gas line 301. The temperature of the catalyst packed bed could be adjusted by varying the voltage applied to the flexible electric heating tape and was maintained at 145-150° C. The products produced in the bed were passed through a bubbler of concentrated sulfuric acid 311. The gas exiting the bubbler was combined with acetylene from gas tank 312, which were then both bubbled through the reaction mixture. The reaction proceeded at 50-55° C. for several hours, and samples were taken at different intervals for gas chromatography mass spectrometry (GC/MS) analysis.

A liquid phase sample of the reaction product was analyzed with an Agilent GC/MS instrument which consisted of a 6890N gas chromatograph, 5973N quadrupole mass selective detector (MSD) and 7683 autosampler. An aliquot of 0.2 μL sample was injected into the GC with 7683 autosampler, and the injector was maintained at 250° C. with a split ratio of 100:1. Compounds were separated using a Phenomenex Zebron ZB-WAX-Plus column (100% polyethylene glycol) that was 30 m length with a 250 μm I.D. and 0.25 μm film thickness (Phenomenex Torrance, Calif., USA). The carrier gas was helium and was set at a constant flow rate of 1.0 mL/min with a head pressure of 7.1 psi at 40° C. The transfer line was set at 280° C. The column oven temperature was programmed from 40° C. to 200° C. with a ramping rate of 20° C./min. Mass selective detection was performed at 230° C. with full scan (15-300 amu) for identification.

Figure 11:
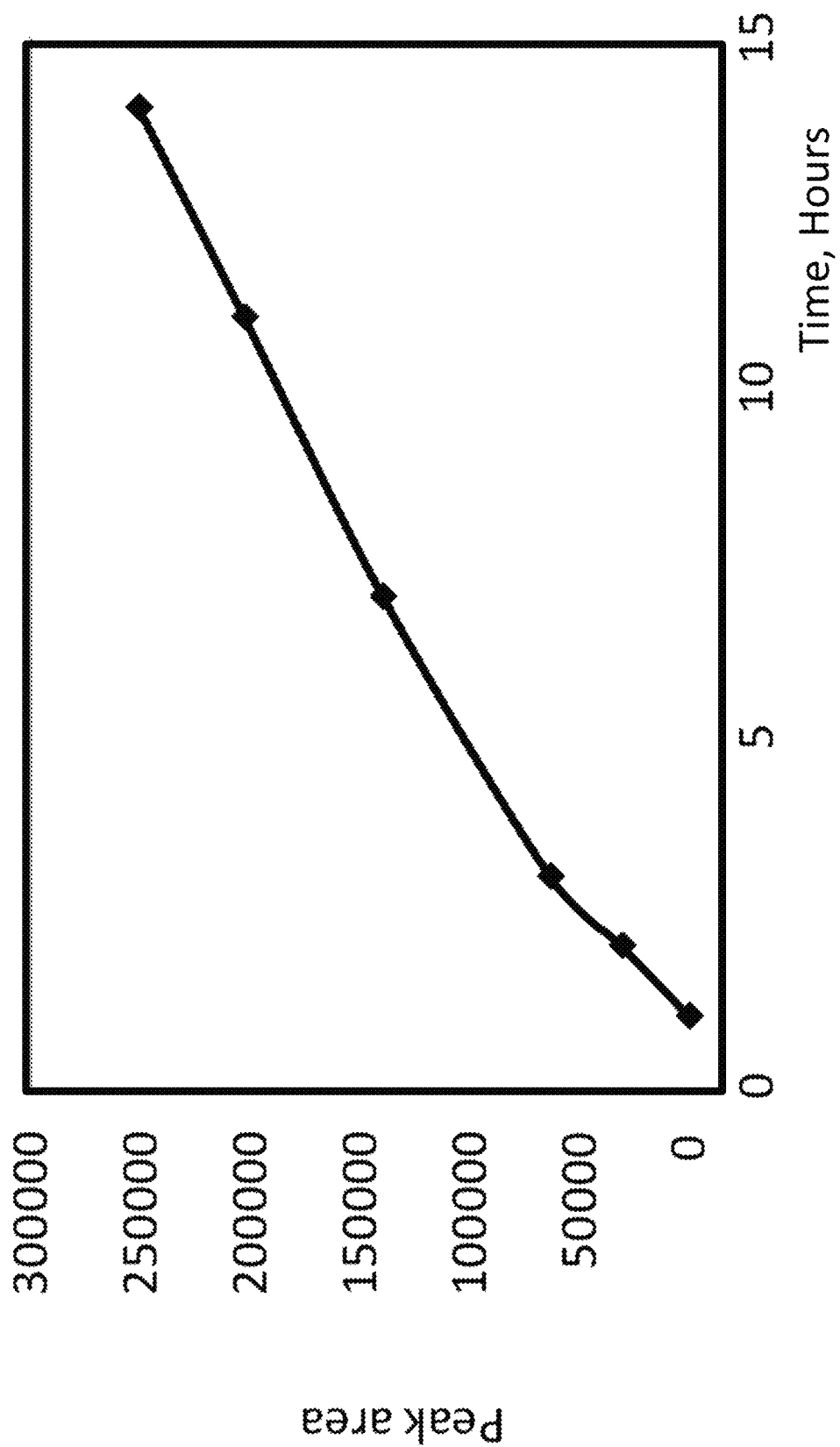
FIG. 11 is a plot showing the growth of the acrylic acid GC peak during the experiments described in Example 6 herein.

After 80 minutes reaction time, acrylic acid was identified in the liquid phase. FIG. 11 illustrates the growth of the acrylic acid peak area, and shows that significant quantities of acrylic acid can be formed. Example 6 thus illustrates the manufacturability of acrylic acid or its derivatives from acetylene and formic acid under mild conditions.

Additional experiments have been performed to identify the effects of varying reaction conditions. It has been found that the reaction occurs as long as the packed bed temperature is at least 100° C. and proceeds with even higher yields when the packed bed temperature is at least 140° C.

The data here were taken using a palladium acetate catalyst. However, Tang et al. (Catalysis Letters 129, pages 189-193 (2009)) demonstrated that reaction (6) is more selective on a mixed copper bromide, nickel acetate catalyst, while Kiss (Chem. Rev. 101 (11), pages 3435-3456 (2001), Jayasree, et al. (Catalysis Letters 58, pages 213-216 (1999)), Drent, et al. (Journal Of Organometallic Chemistry 475, pages 57-63 (1994)) and Brennführe et al. (Chem. Cat. Chem. 1, pages 28-41 (2009)) propose that other palladium based catalysts are preferred for reaction (6). It could be expected that these catalysts would also be useful for reaction (7) above.

Kiss (Chem. Rev. 101 (11), pages 3435-3456 (2001)) and Brennführe et al. (Chem Cat Chem. 1, pages 28-41 (2009)) teach that one can make a large number of organic acids by replacing the acetylene in reaction (6) with an alkene or a different alkyne to yield an organic acid with 3 or more carbons. It is anticipated that formic acid, rather than CO and water, could be successfully employed as a reactant using similar chemistry. For example, the reaction with ethylene is expected to yield propionic acid. The reaction with methylacetylene (propyne) is expected to yield methyl acrylic acid (MAA).

Example 7

Conversion of Formic Acid to Hydrogen

Figure 12:
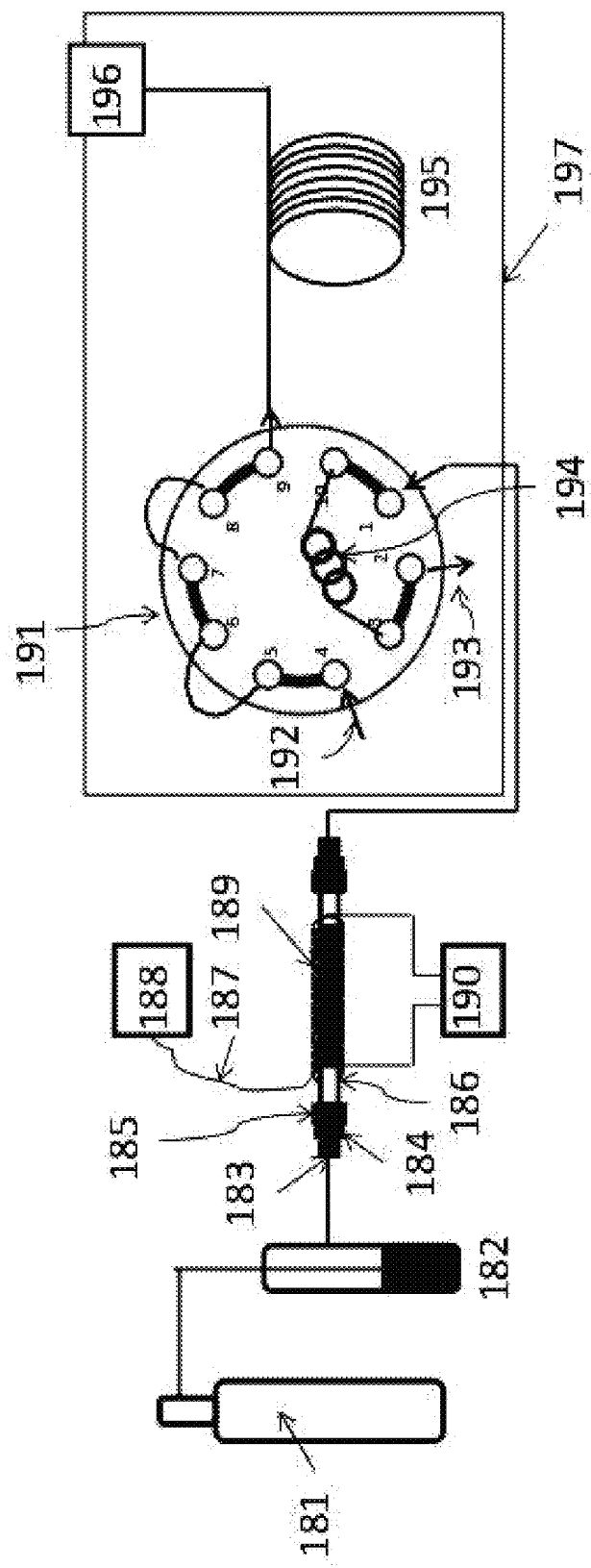
FIG. 12 is a schematic diagram of the apparatus employed in Examples 7 and 8 herein.

Example 7 illustrates the conversion of formic acid to hydrogen and $CO_2$ via reaction (1) above, consistent with the teachings in the Sabatier Paper. The experimental apparatus for Example 7 is shown in FIG. 12. Catalyst packed bed 186 was constructed from a glass tube. A K-type thermocouple 187 was held snugly against the outer glass wall with black tape, and Chromel wire heater 189 (0.31 mm diameter) was coiled around the glass tube to create a heated region. The temperature of catalyst packed bed 186 was measured with a thermocouple thermometer 188 (Barnant 100, Barnant Company, Barrington, Ill., USA). A dual output DC power supply 190 (Agilent, E3647A) was used to heat the Chromel wire heater 189. One side of the catalyst packed bed 186 was connected to a bubbler 182 that contained formic acid with a 1/16 inch nut 183, a 1/16 inch to 1/8 inch reducing union 184, a 1/8 inch nut 185 and 1/8 inch Tygon tubing. The other side of catalyst packed bed 186 was connected to a 1 ml 10-port valve sampling loop 194. The upstream and downstream connections of a molecular sieve 5A packed bed column 195 (length=6 feet; inside diameter=8 inches) were connected with a 10-port valve 191 and a thermal conductivity detector 196, respectively. 10-port valve 191 and the packed column 195 were placed into an SRI 8610C GC 197. Nitrogen from a gas tank 181 was bubbled through a bubbler 182 to carry the formic acid vapor through the catalyst packed bed 186. The flow rate through the column was controlled with an 8610C GC built-in electronic pressure controller module.

Prior to the experiments in Example 7, the palladium catalyst (5% on alumina pellets; available from Alfa Aesar, Ward Hill, Mass.), was conditioned in a box oven (Lindberg/Blue M from Thermo Electron Corporation, now Thermo Fisher Scientific, Waltham, Mass., USA) at 300° C. for 4 hours and granulated to 20-100 mesh particles before packing.

A Pyrex glass tube was cleaned with acetone (certified ACS grade from Fisher Scientific, Pittsburgh, Pa.), and then rinsed with Millipore filtered water (Millipore Corporation, Billerica, Mass., USA) and dried at 100° C. before catalyst packing. The catalyst packed bed was prepared by pouring 0.15 grams of catalyst into a glass tube with shaking or tapping. The tube was first positioned vertically against the workbench, the lower end of the tube was filled with quartz wool (serving as a frit to hold catalyst particles) and the upper end was attached to a funnel into which the solid catalysts are fed. The shaking or tapping reduced voids in the tube and facilitated tight packing. Before the performance test the packed bed column was purged with nitrogen saturated with formic acid vapor at room temperature for 1 to 2 hours.

Experiments were performed on an SRI 8610C gas chromatograph equipped with a thermal conductivity detector (TCD). Formic acid (Fluka, ~98% from Sigma Aldrich, St. Louis, Mo.) vapor was introduced into the catalyst packed bed by nitrogen gas, which also served as carrier gas for column separation and reference gas for the TCD. The temperature of the catalyst packed bed could be adjusted by varying the voltage applied to the Chromel wire heater. The products from the catalyst bed were separated using a molecular sieve 5A packed column (length=6 feet, OD=1/8 inch, from Restek, Bellefonte, Pa.) and detected with TCD. The carrier gas was nitrogen and was set at 10 psi. The column oven temperature was set at 100° C. isothermal for the separation. The temperature of the TCD was maintained at 116° C. Chromatographic data were collected and evaluated using PeakSimple Software (version 4.07, available as a free download from various sources). Error! Reference source not found. below lists the hydrogen peak area from the Pd catalyst bed at various temperatures. The data show that formic acid is converted to $CO_2$ and hydrogen when the temperature of the catalyst packed bed is between 40 and 63° C.

TABLE 3

Hydrogen peak area from Pd catalyst packed bed at different temperatures

| Catalyst bed temperature (° C.) | Hydrogen peak area from TCD |
|---|---|
| 25.2 | 0 |
| 40 | 145 |
| 63.5 | 121 |

The data here were taken on a palladium catalyst, but Ojeda and Iglesia (Angew. Chem. 121, pages 4894-4897 (2009)) claim that nano-gold is preferred. Indeed reaction (1) above has been previously observed on Cr, Fe, Co, Ni, Cu, Ru, Rh, Pd, Ag, Re, Os, Ir, Pt, Au, Pb, Bi, and Sb Example 8

Conversion of Formic Acid to Carbon Monoxide

Example 8 demonstrates that formic acid can be converted to CO and water via reaction (2), consistent with the Sabatier Paper. The procedure follows closely the work of Gates and Schwab (J. Catalysis 15(4), pages 430-434 (1969)).

The apparatus employed in Example 8 is shown in FIG. 12. A Pyrex glass tube (7 inch length, 6 mm OD, 4 mm ID) was cleaned with acetone (certified ACS from Fisher Scientific), and then rinsed with Millipore filtered water (Millipore Corporation, Billerica, Mass., USA) and dried at 100° C. before catalyst packing. The catalyst packed bed was prepared by pouring 1.3 gram of catalyst (trade designation "Dowex 50WX8 hydrogen form", 50-100 mesh (Sigma-Aldrich)) into a glass tube with shaking or tapping. The tube was first positioned vertically against the workbench, the lower end of the tube was filled with quartz wool (serving as a frit to hold catalyst particles) and the upper end was attached with a funnel into which the solid catalysts were fed. The shaking or tapping reduced voids in the tube and facilitated tight packing. Before the performance test the packed bed column was conditioned at 120-150° C. under helium for 3 hours.

Experiments were performed on an SRI 8610C gas chromatograph equipped with a thermal conductivity detector (TCD.) Formic acid (98-100%, Sigma Aldrich, St. Louis, Mo.) vapor was introduced into the catalyst packed bed by helium gas which also served as the carrier gas for column separation and the reference gas for the TCD. The temperature of the catalyst packed bed was adjustable by varying the voltage applied to the Chromel wire heater. The products from the catalyst bed were separated using a molecular sieve 5A packed column (6 feet length, 1/8 inch OD, from Restek) and detected with the TCD. The carrier gas was helium at 10 psi. The column oven temperature was set at 100° C. isothermal for the separation. The temperature of the TCD was maintained at 116° C. Chromatographic data were collected and evaluated using PeakSimple Software (version 4.07).

Figure 13:
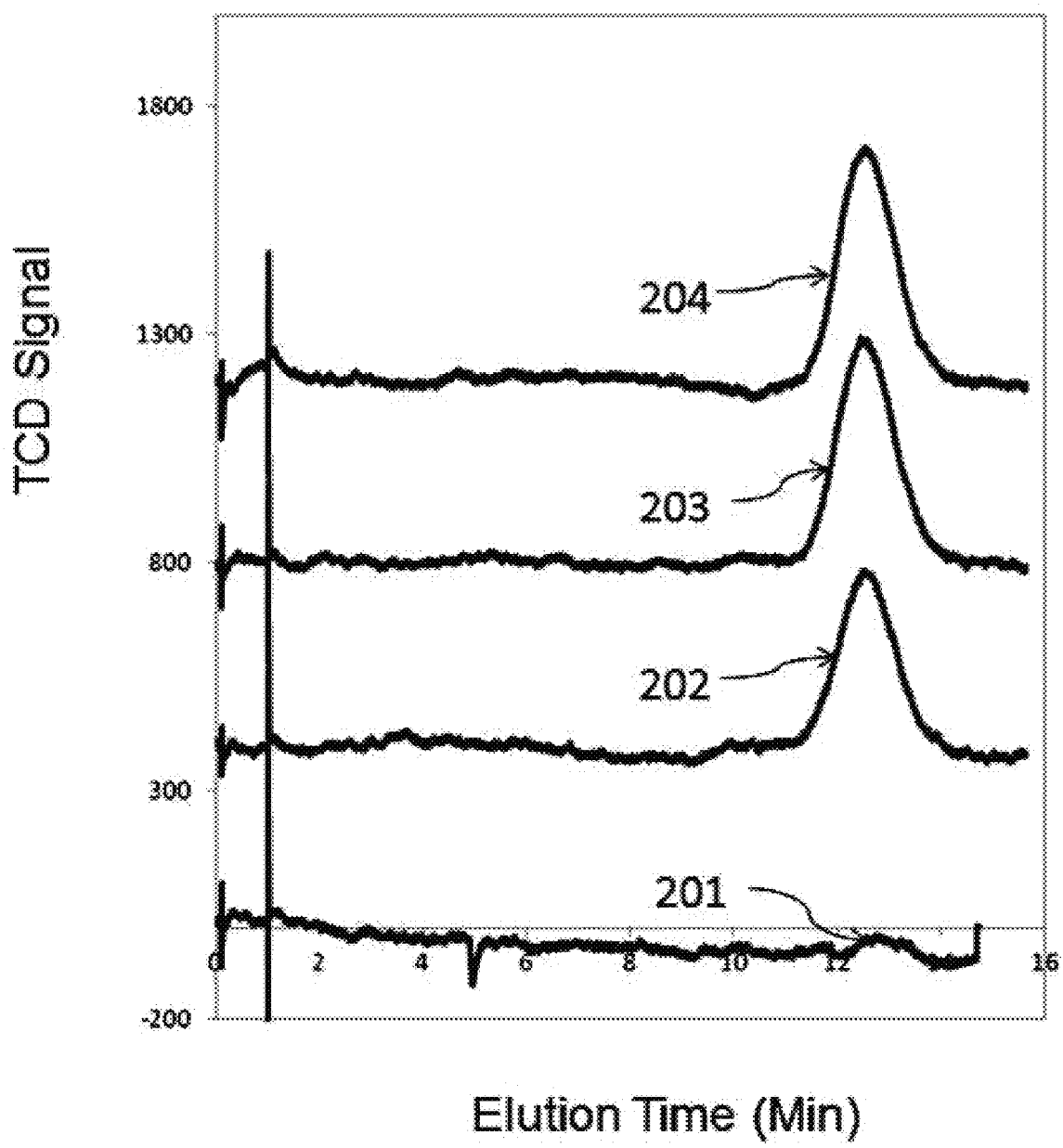
FIG. 13 are GC traces of the conversion of formic acid to CO on a catalyst available under the trade designation Dowex 50WX8, following the procedures described in Example 8 herein.

FIG. 13 shows the chromatogram of the product of formic acid through the catalyst bed at different temperatures. Peak 201 denotes formic acid saturated helium through catalyst packed bed with bed temperature at 100° C. Peak 202 denotes formic acid saturated helium through catalyst packed bed with bed temperature at 130° C. Peak 203 denotes formic acid saturated helium through catalyst packed bed with bed temperature at 168° C. Peak 204 denotes a trace of pure carbon monoxide from a gas bottle It should be noted that no CO is detected at a bed temperature of 100° C., but a CO peak is observed when the catalyst bed temperature is greater than 130° C. This result shows clearly that formic acid can be converted to CO via reaction (2) above.

Example 8 represents one example of a process to form carbon monoxide, but the reviews of Trillo, et al. (Catalysis Reviews 7(1), pages 51-86 (1972)) and Mars (Advances in Catalysis 14, pages 35-113 (1963)) indicate that formic acid decomposes to CO and water on most acidic metal oxides. Mineral acids, such as sulfuric acid and nitric acid, have also been reported to catalyze the reaction.

Example 9

Conversion of Formic Acid to Syngas

Example 9 demonstrates that formic acid can be converted to syngas. The procedure is as follows: The hydrogen produced in Example 7 is mixed with the carbon monoxide produced in Example 8 in a volumetric ratio of three parts hydrogen to one part carbon monoxide to yield syngas.

Persons familiar with the technology involved here will recognize that once syngas is produced, one can make a wealth of compounds including fuels and chemicals, such as methanol (see FIG. 1) or methane (using the Sabatier methanation reaction). The present process encompasses the production of hydrocarbon fuels from formic acid.

While particular elements, embodiments and applications of the present invention have been shown and described, it will be understood that the present invention is not limited thereto, since modifications can be made by those skilled in the art without departing from the scope of the present disclosure, particularly in light of the foregoing teachings.

What is claimed is:

1. A catalytic process for the production of formaldehyde comprising hydrogenating an amount of formic acid to form a product comprising formaldehyde, wherein said formaldehyde is formed without hydrogenating more than 10% of said amount of formic acid to methanol, wherein the process is catalyzed by a catalyst comprising at least one of Ce (IV) oxide and Te (IV) oxide.

2. The catalytic process of claim 1, further comprising initially converting an amount of carbon dioxide obtained from a natural source or from an artificial chemical source to produce said amount of formic acid, thereby reducing said amount of carbon dioxide present in nature or diverting said amount of carbon dioxide from being discharged into the environment by said artificial chemical source.

3. The catalytic process of claim 1, wherein reaction temperature is between 8° C. and 350° C.

4. The catalytic process of claim 3, wherein said reaction temperature is between 40° C. and 200° C.

5. The catalytic process of claim 4, wherein said reaction temperature is between 60° C. and 100° C.

* * * * *